United States Patent [19]
Gully et al.

[11] Patent Number: 5,880,135
[45] Date of Patent: Mar. 9, 1999

[54] SUBSTITUTED 4-PHENYLAMINOTHIAZOLES, THEIR PROCESS OF PREPARATION AND THE PHARMACEUTICAL COMPOSITIONS CONTAINING THEM

[75] Inventors: Danielle Gully, Muret; Pierre Roger, Montigny Le Bretonneux; Camille Georges Wermuth, Strasbourg, all of France

[73] Assignee: Sanofi, Paris, France

[21] Appl. No.: 945,098

[22] PCT Filed: Jun. 18, 1996

[86] PCT No.: PCT/FR96/00941

§ 371 Date: Dec. 22, 1997

§ 102(e) Date: Dec. 22, 1997

[87] PCT Pub. No.: WO97/00868

PCT Pub. Date: Jan. 9, 1997

[30]  Foreign Application Priority Data

Jun. 21, 1995 [FR] France ................................. 95 07437

[51] Int. Cl.⁶ ...................... C07D 277/42; C07D 417/12; A61K 31/425
[52] U.S. Cl. .......................... 514/307; 514/310; 514/311; 514/313; 514/394; 514/249; 514/257; 514/414; 514/370; 546/143; 546/148; 546/159; 546/167; 548/190; 548/304.7; 548/465; 544/235; 544/353; 544/356
[58] Field of Search ................................ 546/152, 143, 546/148, 159, 167; 514/314, 299, 257, 307, 310, 311, 313, 370, 394, 414; 548/100, 465, 304.7; 544/235, 353, 356

[56]  References Cited

FOREIGN PATENT DOCUMENTS

WO91/09857  7/1991  WIPO .

*Primary Examiner*—Zinna Northington Davis
*Attorney, Agent, or Firm*—Jacobson, Price, Holman & Stern, PLLC

[57]  ABSTRACT

A compound, as well as its stereoisomers and addition salts, posssssing antagonist activity with respect to corticotropin releasing hormone (CRF) has the formula:

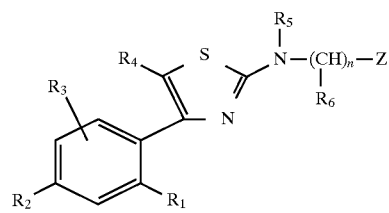

in which $R_1$, and $R_{21}$ which are identical or different, are independently selected from a halogen atom; a $(C_1-C_5)$ hydroxyalkyl radical; a $(C_1-C_5)$alkyl; a $(C_7-C_{10})$aralkyl; a $(C_1-C_5)$alkoxy; a trifluoromethyl; a nitro; a nitrile; an —SR group in which R is selected from hydrogen, a $(C_1-C_5)$alkyl radical and a $(C_7-C_{10})$aralkyl radical; an —S—CO—R group in which R is selected from a $(C_1-C_5)$alkyl radical and an aralkyl radical in which the aryl part is $(C_6-C_8)$ and the alkyl part is $(C_1-C_4)$; a —COOR' group in which R' is selected from hydrogen and a $(C_1-C_5)$alkyl; a —CONR—R'R" group with R' and R" as defined above for R'; an —NR'R" group with R' and R" as defined above for R'; a —CONRaRb or —NRaRb group in which Ra and Rb constitute, with the nitrogen atom to which they are bonded, a 5- to 7-membered heterocycle; and an —NHCO—NR'R" group with R' and R" as defined above for R'; $R_3$ represents hydrogen or is as defined above for $R_1$ and $R_2$; $R_4$ is selected from a hydrogen atom; a $(C_1-C_5)$alkyl; a halogen, a hydroxymethyl group; and a formyl group; $R_5$ is selected from a $(C_1-C_5)$alkyl; a $(C_3-C_7)$cycloalkyl group; a cycloalkylalkyl group in which the cycloalkyl part is $(C_3-C_7)$ and the alkyl part is $(C_1-C_5)$; and alkenyl containing 5 to 6 carbon atoms; n represents zero or one; $R_6$ is selected from a $(C_1-C_5)$alkyl; an alkoxyalkyl in which the alkyl parts are $(C_1-C_5)$; a $(C_3-C_7)$cycloalkyl; a cycloalkylalkyl group in which the cycloalkyl part is $(C_3-C_7)$ and the alkyl part is $(C_1-C_5)$; a cycloalkyloxyalkyl radical in which the cycloalkyl is $(C_3-C_7)$ and the alkyl part is $(C_1-C_4)$; a hydroxyalkyloxyalkyl radical in which the alkyls are $(C_2-C_{10})$; and an alkoxyalkyloxyalkyl radical in which the alkyls are $(C_3-C_{12})$; Z represents an optionally substituted bi- or tricyclic aromatic or heteroaromatic group.

10 Claims, No Drawings

SUBSTITUTED 4-PHENYLAMINOTHIAZOLES, THEIR PROCESS OF PREPARATION AND THE PHARMACEUTICAL COMPOSITIONS CONTAINING THEM

This application is a §371 of PCT/FR96/00941, filed Jun. 18, 1996.

SUMMARY

The invention relates to substituted aminothiazoles of formula:

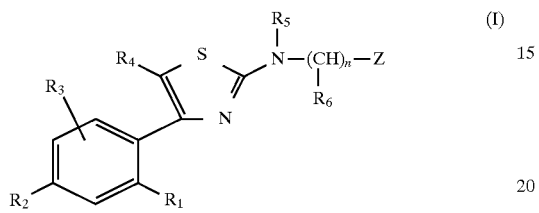

in which $R_1$ to $R_6$, n and Z are as defined in claim 1.

The subject of the present invention is new substituted branched aminothiazoles, and a process for their preparation. These new substituted compounds generally have an antagonist activity with respect to CRF (corticotropin releasing factor) and can therefore constitute active principles of pharmaceutical compositions.

Corticotropin releasing factor (CRF) is a peptide whose sequence of 41 amino acids was characterized by Vale W. et al. in 1981 (Science, 1981, 213, 1394–1397). CRF is the main endogenous factor involved in regulation of the hypothalamohypophysosuprarenal axis (release of adrenocorticotropic hormone: ACTH) and its pathologies, as well as in the depressive syndromes which result therefrom. CRF also causes secretion of β-endorphin, of β-lipotropin and of corticosterone.

CRF is therefore the physiological regulator of the secretion of adrenocorticotropic hormone (ACTH) and more generally of peptides derived from pro-opiomelano-cortin (POMC). Although located in the hypothalamus, CRF is also widely distributed in the central nervous system (limbic area), in which it plays the role of neurotransmitter and/or of neuromodulator, independently of its effects on the hypothalamohypophysosuprarenal axis.

Numerous animal experiments have shown that the central administration of CRF causes varied anxiogenic effects, such as modification of the behaviour in general: for example neophobia, reduction in sexual receptivity and decrease in food consumption and slow-wave sleep in the rat. The intracerebroventricular injection of CRF also increases the excitation of the noradrenergic neurons of the locus coeruleus which is often associated in animals with a state of anxiety. In the rat, the central or peripheral administration of CRF causes modifications in gastric dumping, in intestinal transit time, in faecal excretion and in acid secretion, as well as tensional effects. The specific involvement of CRF in these effects was demonstrated by the use of a peptide antagonist, α-helical CRF(9-41) (ah-CRF), or of specific antibodies (Rivier J. et al., Science, 1984, 224, 889–891), which makes it possible to confirm the role of this peptide in the development of endocrinal and behavioural disorders related to stress.

Indeed, these experiments show that CRF plays an important role in man in the integration of the complex responses observed during physiological, psychological or immunological stress, simultaneously at the neuroendocrinal, visceral and behavioural levels (Morley J. E. et al., Endocrine Review, 1987, 8, 3, 256–287; Smith M. A. et al., Horm. Res., 1989, 31, 66–71). In addition, clinical data militate in favour of the effective involvement of CRF in many disorders resulting from a condition of stress (Gulley L. R. et al., J. Clin. Psychiatry, 1993, 54, 1, (suppl.), 16–19), such as:

- the existence of the CRF test (i.v. administration) in man has made it possible to show the modification in the ACTH response in depressive patients (Breier A. et al., Am. J. Psychiatry, 1987, 144, 1419–1425).
- the discovery of an endogenous CRF hypersecretion in certain pathologies, for example a high level of CRF in the cephalorhachidian fluid in non-medicated patients who are depressed or affected by dementia of Alzheimer's disease type (Nemeroff C. B. et al., Science 1984, 226, 4680, 1342–1343; Regul. Pept., 1989, 25, 123–130) or a decreased density of CRF receptors in the cortex of suicide victims (Nemeroff C. B. et al., Arch. Gen. Psychiatry, 1988, 45, 577–579).
- the dysfunctioning of CRF-dependent neurons is even suggested in the severe pathologies of Alzheimer's and Parkinson's diseases, Huntington's chorea and amyotrophic lateral sclerosis (De Souza E. B., Hospital Practice, 1988, 23, 59).

The central administration of CRF in many animal species produces behavioural effects similar to those obtained in man in stress situations. When they are repeated with time, these effects can result in various pathologies, such as: fatigue syndrome, hypertension, heart disorders, modification in gastric dumping and in faecal excretion (colitis, irritable bowel syndrome), modification in acid secretion, hyperglycaemia, retarded growth, anorexia, neophobia, reproductive disorders, immunosuppression (inflammatory disorders, multiple infections and cancers) and varied neuropsychiatric disorders (depression, anorexia nervosa and anxiety).

The injection via the intracerebroventricular route of the reference peptide antagonist, ah-CRF, prevents the effects obtained either by the administration of exogenous CRF or by the use of stress-inducing agents (ether, restraint, noise, electric shock, ethanol withdrawal symptoms or surgery) capable by themselves of inducing an increase in the level of endogenous CRF. These results are confirmed by the study of many antagonist molecules which are structurally related to CRF and which have a prolonged duration of action with respect to ah-CRF (Rivier J. et al., J. Med. Chem., 1993, 36, 2851–2859; Menzaghi F. et al., J. Pharmacol. Exp. Ther., 1994, 269, 2, 564–572: Hernandez J. F. et al., J. Med. Chem., 1993, 36, 2860–2867). In addition, preliminary studies have shown that tricyclic anti-depressants could modulate the level of CRF and the number of CRF receptors in the brain (Grigoriadis D. E. et al., Neuropsychopharmacology, 1989, 2, 53–60). Likewise, benzodiazepine anxiolytics are capable of reversing the effect of CRF (Britton K. T. et al., Psychopharmacology, 1988, 94, 306), without the mechanism of action of these substances being entirely elucidated. These results confirm, if necessary, the growing need for non-peptide antagonist molecules for CRF receptors.

It is also important to point out three possible consequences of conditions of chronic stress, which are immunodepression, fertility disorders and the development of diabetes.

A large number of substituted 2-aminothiazoles are already known. Patent Application EP 462,264 describes substituted 2-aminothiazoles in which the tertiary amine in the 2-position contains two substituents, each having at least one heteroatom, one of which is a substituted amine. These compounds are antagonists of PAF-acether and are applied in the treatment of asthma, some allergic or inflammatory conditions, cardiovascular diseases, hypertension and various renal pathologies or alternatively as contraceptive agents. Application GB 2,022,285 describes compounds having a regulatory activity for the immune response and having antiinflammatory properties. They are substituted thiazoles which are substituted in the 2-position by secondary amine groups.

Some heterocyclic substituted 2-acylaminothiazoles have been described in Patent Application EP 432,040. These compounds are antagonists of cholecystokinin and of gastrin. Substituted 2-amino-4,5-diphenylthiazoles having antiinflammatory properties are also known (Patent Application JP-01 75 475). Substituted 2-amino-4-(4-hydroxyphenyl) thiazoles are also known which are useful as synthetic intermediates in the preparation of substituted 2,2-diarylchromenothiazoles (Patent Application EP 205,069). Substituted 2-(N-methyl-N-benzylamino)thiazoles are also described in J. Chem. Soc. Perkin, Trans 1, 1984, 2, 147–153 and in J. Chem. Soc. Perkin, Trans 1, 1983, 2, 341–347.

Patent Application EP 283,390 describes, among other substituted thiazoles, substituted 2-(N-alkyl-N-pyridylalkylamino)thiazoles of formula:

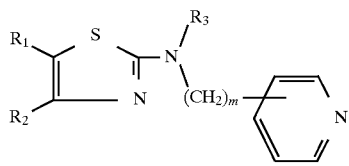

These substituted compounds, in which the amine in the 2-position is substituted by an unbranched pyridylalkyl radical, in particular have an activity which stimulates the central cholinergic transmission. They can therefore be used as antagonists for muscarinic receptors and are applied in the treatment of memory disorders and of senile dementias.

Substituted 2-aminothiazoles in which the amine in the 2-position is a tertiary amine having a branched alkyl or aralkyl substituent have been described in EP 576,350 as having an affinity for CRF receptors.

U.S. Pat. No. 5,063,245 has described a CRF antagonist having a micromolar potency in vitro. Many patent applications relating to non-peptide molecules have subsequently been published, for example Applications WO 94/13643, WO 94/13644, WO 94/13661, WO 94/13676, WO 94/13677, WO 94/10333, WO 95/00640, WO 95/10506, WO 95/13372, WO 95/33727, WO 95/33750, WO 95/34563 or EP 691 128.

It has now been found that some substituted branched aminothiazoles, which are the subject of the present invention, have an excellent affinity with respect to receptors which are specific for CRF. Moreover, on taking into account their structure, these molecules have a good dispersibility and/or solubility in solvents or solutions commonly used in therapeutics, which confers on them an improved pharmacological activity and which also makes possible the easy preparation of oral and parenteral pharmaceutical dosage forms.

The subject of the present invention is the compounds of formula:

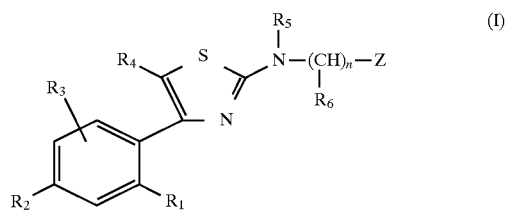

in which $R_1$ and $R_2$, which are identical or different, each independently represent a halogen atom; a $(C_1-C_5)$ hydroxyalkyl radical; a $(C_1-C_5)$ alkyl; a $(C_7-C_{10})$ aralkyl; a $(C_1-C_5)$ alkoxy; a trifluoromethyl; a nitro; a nitrile; an —SR group in which R represents hydrogen, a $(C_1-C_5)$ alkyl radical or a $(C_7-C_{10})$ aralkyl radical; an —S—CO—R group in which R represents a $(C_1-C_5)$ alkyl radical or an aralkyl radical in which the aryl part is $(C_6-C_8)$ and the alkyl part is $(C_1-C_4)$; a 13 COOR' group in which R' represents hydrogen or a $(C_1-C_5)$ alkyl; a —CONR'R" group with R' and R" as defined above for R'; an —NR'R" group with R' and R" as defined above for R'; a —CONRaRb or —NRaRb group in which Ra and Rb constitute, with the nitrogen atom to which they are bonded, a 5- to 7-membered heterocycle; or an —NHCO—NR'R" group with R' and R" as defined above for R';

$R_3$ represents hydrogen or is as defined above for $R_1$ and $R_2$;

$R_4$ represents a hydrogen atom; a $(C_1-C_5)$ alkyl; a halogen; a hydroxymethyl group; or a formyl group;

$R_5$ represents a $(C_1-C_5)$ alkyl; a $(C_3-C_7)$ cycloalkyl group; a cycloalkylalkyl group in which the cycloalkyl is $(C_3-C_7)$ and the alkyl is $(C_1-C_5)$; or an alkenyl containing 5 to 6 carbon atoms;

n represents zero or one;

$R_6$ represents a $(C_1-C_5)$ alkyl; an alkoxyalkyl in which the alkyls are $(C_1-C_5)$; a $(C_3-C_7)$ cycloalkyl; a cycloalkylalkyl group in which the cycloalkyl is $(C_3-C_7)$ and the alkyl is $(C_1-C_5)$; a cycloalkyloxyalkyl radical in which the cycloalkyl is $(C_3-C_7)$ and the alkyl is $(C_1-C_4)$; a hydroxyalkyloxyalkyl radical in which the alkyls are $(C_2-C_{10})$; or an alkoxyalkyloxyalkyl radical in which the alkyls are $(C_3-C_{12})$;

Z represents an optionally substituted bi- or tricyclic aromatic or heteroaromatic group; their stereoisomers and/or their addition salts.

Bi- or tricyclic aromatic or heteroaromatic group is understood to mean particularly a $(C_{10}-C_{14})$ bi- or tricyclic aryl group or a $(C_5-C_{13})$ bi- or tricyclic heteroaryl group comprising 1 to 5 heteroatoms chosen from N, S and O; the said groups preferably being selected from naphthalene, quinoline, isoquinoline, quinoxaline, quinazoline, cinnoline, phthalazine, 1,5 -naphthyridine, 1,7-naphthyridine, indole, isoindole, benzothiophene, benzofuran, benzimidazole, indane, ixidazole, quinolizine, pyridopyrimidine, pyrrolopyrimidine or pyrazolopyrimidine; it being possible for the said groups optionally to be substituted.

The substituents of the Z group are preferably selected from halogen, $(C_1-C_3)$ alkyl, $(C_1-C_3)$ alkoxy, trifluoromethyl, nitro, —NRdRe with Rd and Re independently representing hydrogen or a $(C_1-C_3)$ alkyl, alkoxycarbonylalkyl, carboxyalkyl, morpholinocarbonylalkyl, alkylcarbonylalkyl, dialkylaminocarbonylalkyl or alkoxyalkoxy in which the alkyls are $(C_1-C_3)$.

In the present description, the alkyl groups or the alkoxy groups are linear or branched.

Advantageous compounds according to the invention are those in which Z represents a naphthyl group or a heteroaromatic group selected from quinolyl, isoquinolyl, quinazolyl, quinoxalyl, indolyl or indazolyl, the said groups optionally being substituted, $R_1$, $R_2$, $R_3$, $R_4$, $R_5$, n and $R_6$ being as defined for (I), one of their stereoisomers and/or one of their salts.

Preference is given to those in which $R_3$ represents hydrogen, $R_4$ represents a methyl, $R_5$ represents a propyl, n is 0 and $R_1$, $R_2$ and Z are as defined for (I), one of their stereoisomers and/or one of their salts.

Preference is particularly given to the compounds in which $R_3$ represents hydrogen, $R_4$ represents a methyl, $R_5$ represents a propyl, n is 1, $R_6$ represents a cyclopropyl and $R_1$, $R_2$ and Z are as defined for (I), one of their stereoisomers and/or one of their salts.

Preference is also particularly given to the compounds in which $R_3$ represents hydrogen, $R_4$ represents a methyl, $R_5$ represents a propyl, n is 1, $R_6$ represents a methoxymethyl radical and $R_1$, $R_2$ and Z are as defined for (I), one of their stereoisomers and/or one of their salts.

Preference is more particularly given to the compounds (I) in which $R_3$ represents hydrogen, $R_4$ represents a methyl, $R_5$ represents a propyl and $R_1$ or $R_2$ represents a halogen or a ($C_1$–$C_5$) alkyl or alkoxy; n, $R_6$ and Z being as defined for (I), one of their stereoisomers and/or one of their salts.

Preference is also more particularly given to the compounds:

4-(2,4-dichlorophenyl)-5-methyl-2-[N-(1-(methoxymethyl)-1-(naphth-2-yl)methyl)-N-propylamino]thiazole (Example 3), 4-(2,4-dichlorophenyl)-5-methyl-2-[N-(6-methoxyisoquinol-5-yl)-N-propylamino]thiazole oxalate (Example 4), 4-(2-chloro-4-methoxyphenyl)-5-methyl-2-[N-(6-methylisoquinol-5-yl)-N-propylamino]thiazole oxalate (Example 5), 4-(2-chloro-4-methoxyphenyl)-5-methyl-2-[N-(1-methoxycarbonylmethylindol-5-yl)-N-propylamino]thiazole (Example 9), 4-(2-chloro-4-methoxyphenyl)-5-methyl-2-[N-(6-methoxyisoquinol-5-yl)-N-propylamino] thiazole oxalate (Example 27), 4-(2-chloro-4-methoxyphenyl)-5-methyl-2-[N-(6-chloroisoquinol-5-yl)-N-propylamino]thiazole oxalate (Example 29), 4-(2-chloro-4-methoxyphenyl)-5-methyl-2-[N-(6-methoxyisoquinol-5-yl)-N-propylamino]thiazole oxalate (Example 31), 4-(2-chloro-4-methoxyphenyl)-5-methyl-2-[N-(1-methoxynaphth-2-yl)-N-propylamino]thiazole (Example 34), 4-(2-chloro-4-trifluoromethylphenyl)-5-methyl-2-[N-(6-methoxyisoquinol-5-yl)-N-propylamino]thiazole oxalate (Example 37), 4-(2-chloro-4-methoxyphenyl)-5-methyl-2-[N-(2-ethoxynaphth-1-yl)-N-propylamino]thiazole hydrochloride (Example 40), 4-(2-chloro-4-methoxyphenyl)-5-methyl-2-[N-(2,3-dimethylnaphth-1-yl)-N-propylamino]thiazole hydrochloride (Example 44), 4-(2-chloro-4-methoxyphenyl)-5-methyl-2-[N-(6-bromo-2-methoxynaphth-1-yl)-N-propylamino]thiazole hydrochloride (Example 45), 4-(2-chloro-4-methoxyphenyl)-5-methyl-2-[N-(2,6-dimethylnaphth-1-yl)-N-propylamino]thiazole hydrochloride (Example 46), 4-(2-chloro-4-methoxyphenyl)-5-methyl-2-[N-(1-(methoxymethyl)-1-(naphth-2-yl)methyl)-N-propylamino]thiazole hydrochloride (Example 53), 4-(2-chloro-4-methoxyphenyl)-5-methyl-2-[N-(1-(cyclopropyl)-1-(naphth-2-yl)methyl)-N-propylamino]thiazole hydrochloride (Example 61), one of their stereoisomers and/or optionally one of their salts.

The compounds of the invention in the free form generally exhibit basic properties. However, depending on the nature of the substituents, some may exhibit acid properties.

The salts of the compounds of formula (I) with pharmaceutically acceptable acids or bases (when this is possible) are the preferred salts but those which can make it possible to isolate the compounds of formula (I), in particular for purifying them or for obtaining pure isomers, are also within the invention.

Mention may be made, among acids which are pharmaceutically acceptable for the preparation of the addition salts with the compounds of formula (I), of hydrochloric, phosphoric, fumaric, citric, oxalic, sulphuric, ascorbic, tartaric, maleic, mandelic, methanesulphonic, lactobionic, gluconic, glucaric, succinylsulphonic and hydroxypropanesulphonic acids and the like.

Mention may be made, among bases which are pharmaceutically acceptable for the preparation of the addition salts with the compounds of formula (I) when the latter have acid properties, of sodium hydroxide, potassium hydroxide, ammonium hydroxide, and the like.

The compounds according to the invention and the intermediates are prepared according to methods which are well known to the person skilled in the art, in particular according to EP 576,350.

The following reaction scheme illustrates the preparation process used for the synthesis of the compounds (I).

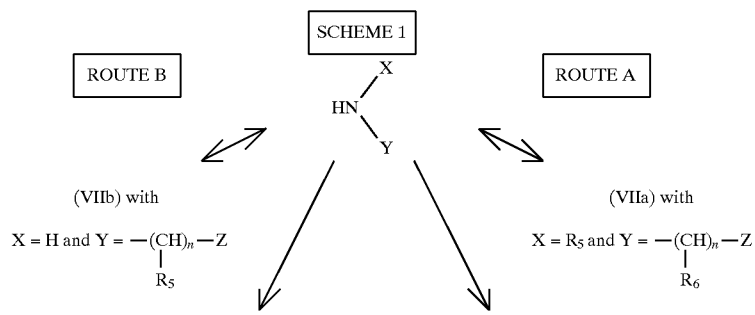

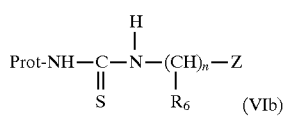
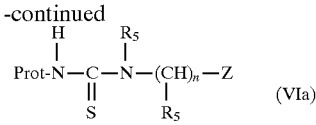

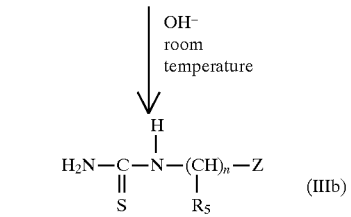
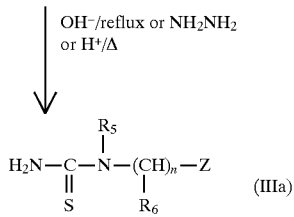

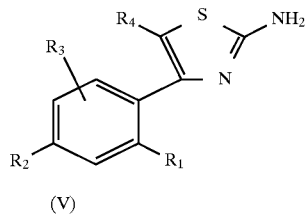
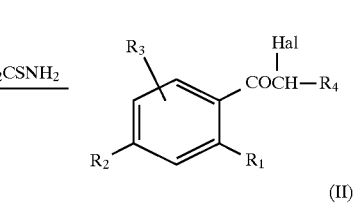

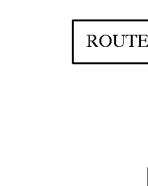

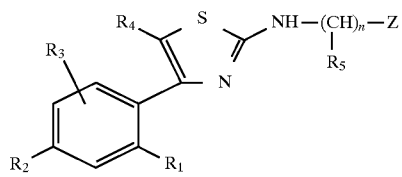
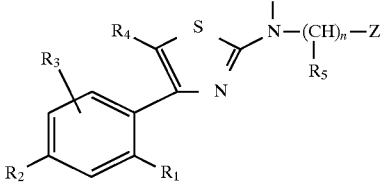

Reaction schemes 2, 3 and 4 illustrate, as examples, the synthesis of specific compounds of formula (I) via Routes A, B and C.

The synthesis of the intermediates is described in detail in the PREPARATIONS; that of the compounds (I) according to the invention is described in the EXAMPLES and in the TABLES below.

SCHEME 2: ROUTE A
4-(2-Chloro-4-methoxyphenyl)-5-methyl-2-[N-naphth-1-yl-N-propylamino]thiazole

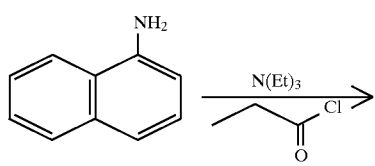

-continued

SCHEME 2: ROUTE A
4-(2-Chloro-4-methoxyphenyl)-5-methyl-2-[N-naphth-1-yl-N-propylamino]thiazole

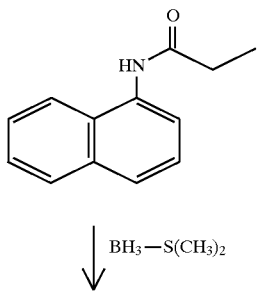

SCHEME 2: ROUTE A
4-(2-Chloro-4-methoxyphenyl)-5-methyl-2-[N-naphth-1-yl-N-propylamino]thiazole
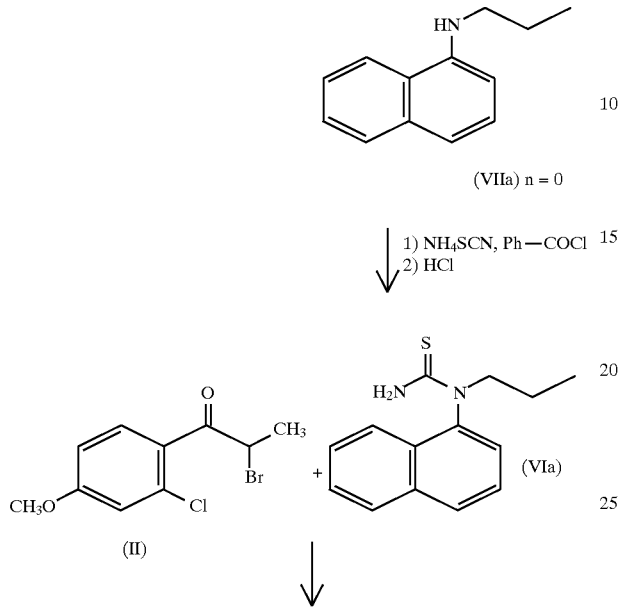
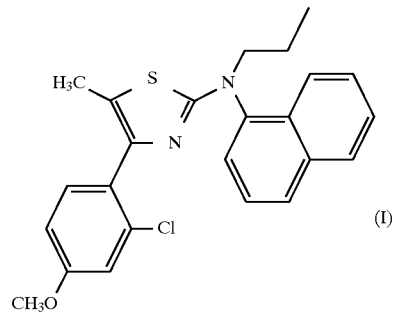
SCHEME 3: ROUTE B
4-(2,4-Dichlorophenyl)-5-methyl-2-[N-(6-methylisoquinol-5-yl)-N-propylamino]thiazole oxalate
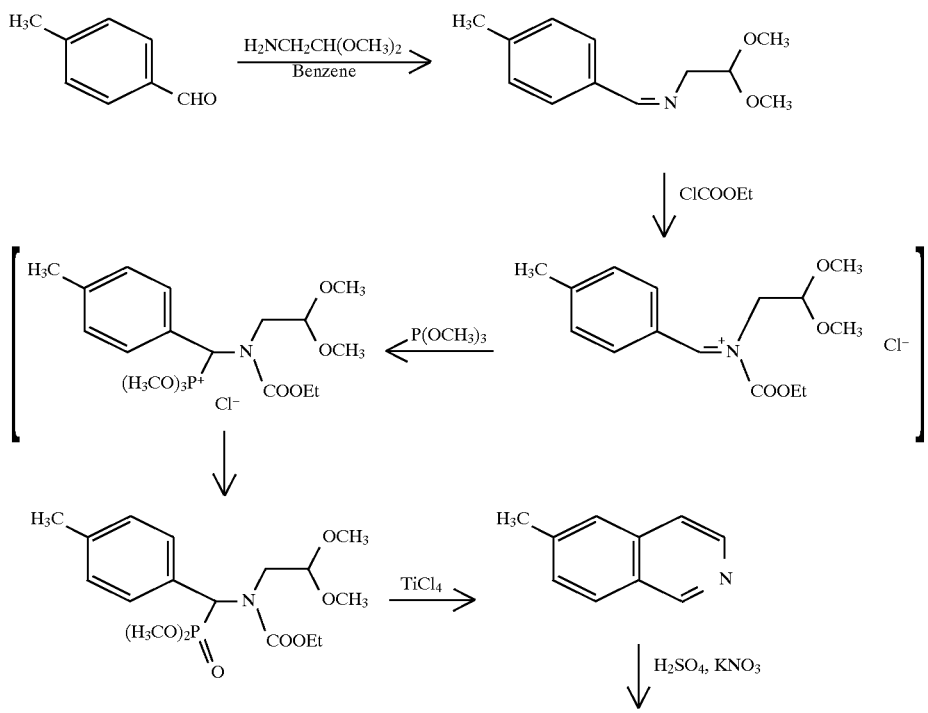

SCHEME 3: ROUTE B
4-(2,4-Dichlorophenyl)-5-methyl-2-[N-(6-methylisoquinol-5-yl)-N-propylamino]thiazole oxalate
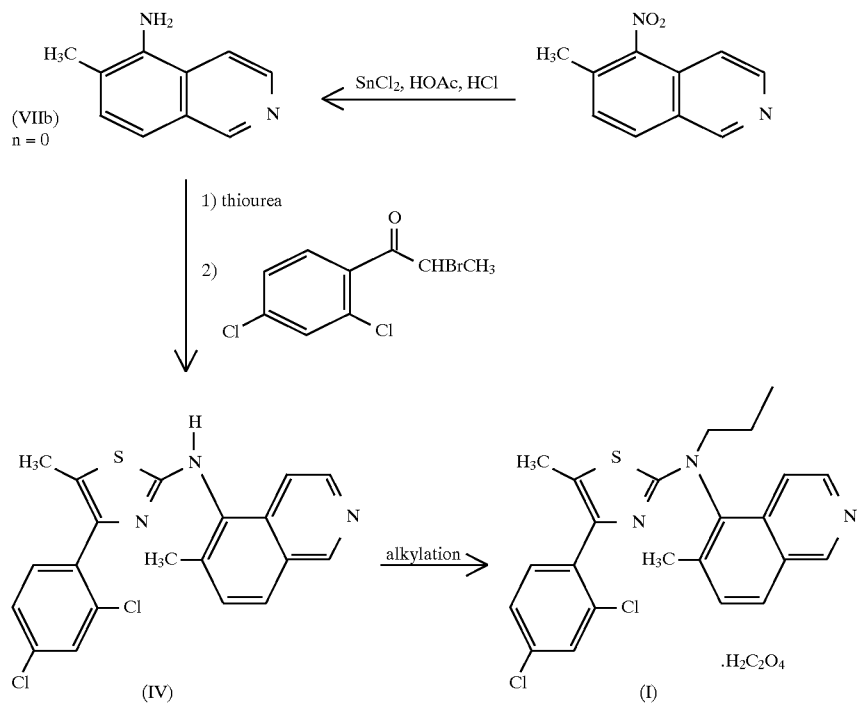
SCHEME 4: ROUTE C
4-(2,4-Dichlorophenyl)-5-methyl-2-[N-(1-(cyclopropyl)-1-(quinol-4-yl)methyl)-N-propylamino]thiazole oxalate
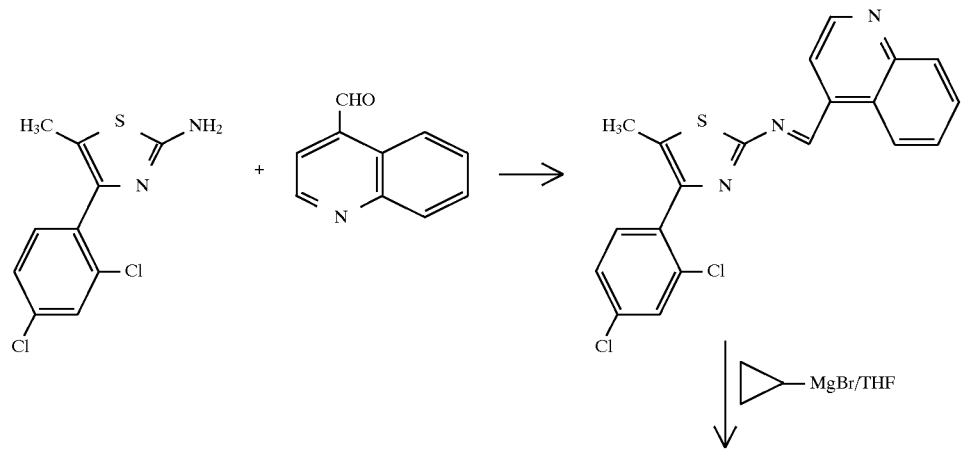

-continued
SCHEME 4: ROUTE C
4-(2,4-Dichlorophenyl)-5-methyl-2-[N-(1-(cyclopropyl)-
1-(quinol-4-yl)methyl)-N-propylamino]thiazole oxalate

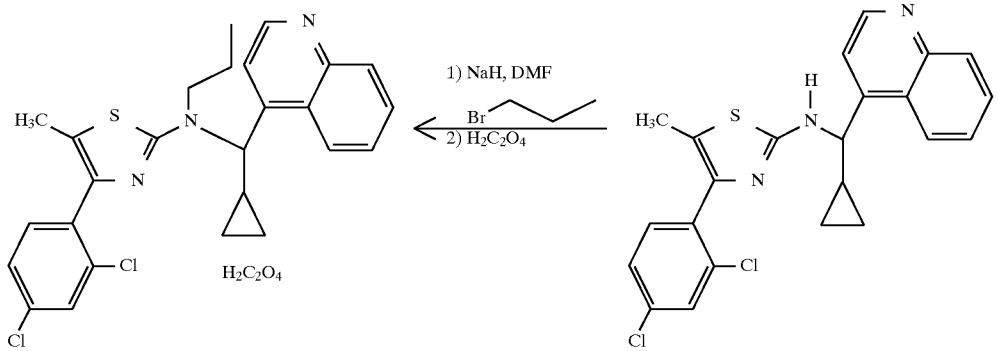

Also within the present invention is a process for the preparation of the compounds of formula (I), characterized in that a substituted α-halogenated compound, preferably α-brominated or α-chlorinated, of formula (II)

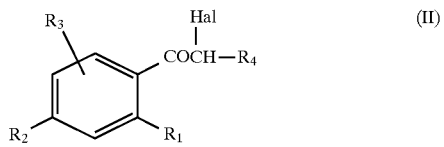

in which $R_1$, $R_2$, $R_3$, Hal and $R_4$ are as defined for (I), is reacted either with a thiourea (ROUTE B) of formula:

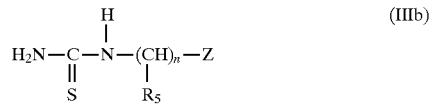

in which $R_5$ and Z are as defined for (I), to obtain a compound of formula (IV)

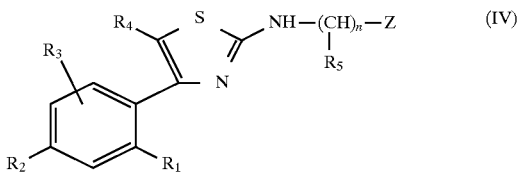

in which $R_1$, $R_2$, $R_3$, $R_4$, n, $R_5$ and Z are as defined for (I), in order to subsequently subject it to an alkylation reaction in order to provide the compound (I) and to obtain, in particular in the case where Z represents a nitrogenous heterocycle, such as indole or indazole, —either monoalkylated compounds, the reactive nitrogen of the ring being first substituted by a protective group, preferably of tetrahydropyranyl type, —or dialkylated compounds,, the freed reactive nitrogen being alkylated after deprotection of the ring of the monoalkylated compound obtained, it being possible for these dialkylated compounds, depending on the nature of the second alkyl group, to result in dialkylated products having different or identical alkyl groups, it being possible, in the latter case, for these compounds also to be obtained directly by dialkylation from compound (IV) in which the reactive nitrogen of the heterocycle is not protected, or with a thiourea (ROUTE A) of formula

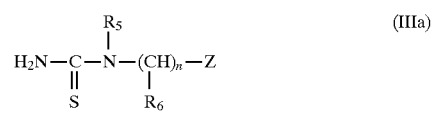

in which $R_5$, n, $R_5$ and Z are as defined for (I), to result directly in the compound (I)

or with thiourea (ROUTE C), to result in the aminothiazole of formula

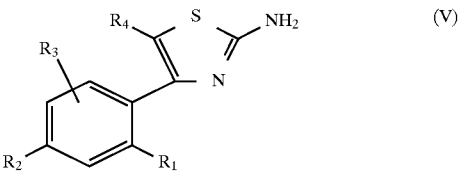

in which $R_1$, $R_2$, $R_3$ and $R_4$ are as defined for (I), which is then optionally reacted with an aldehyde of formula HCO-Z in order to obtain an imine which, by reacting with an organomagnesium compound or an organolithium compound of formula $R_5Li$ or $R_5MgX$ (where X is a halide), results in a compound of formula (IV) which alkylated, for example by reacting with a compound of formula $R_5X$ (where X is a leaving group, such as a halide), to obtain the compound (I) and, if appropriate, the compounds of formula (I) thus obtained are then optionally separated into their possible stereoisomers and/or salified to form the corresponding salts.

The alkylation reactions used in the above process are carried out, under the usual conditions known to the person skilled in the art, using an appropriate alkylating agent, such as, for example, an alkyl halide.

The substituted compounds of formula (II) can be obtained from the corresponding non-halogenated ketones of formula

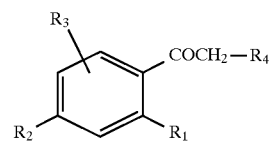

either by reacting with bromine in an appropriate organic solvent, such as acetic acid, carbon tetrachloride or diethyl ether, or by reacting with quaternary ammonium tribromides, according to the method described in Bull. Chem. Soc. Japan, 1987, 60, 1159–1160 and 2667–2668, or alternatively by reacting with cupric bromide in an organic solvent, such as a mixture of chloroform and ethyl acetate, according to J. Org. Chem., 1964, 29, 3451–3461.

As an alternative, the compounds of formula (II) can be obtained by reacting 2-bromopropionyl bromide with a substituted benzene of formula

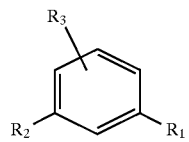

by a Friedel-Crafts reaction.

The ketones are generally known products or products which are commercially available. These compounds can be prepared by a Friedel-Crafts reaction in the presence of a Lewis acid, according to methods well known to the person skilled in the art.

The substituted thioureas (IIIa) and (IIIb) are obtained from the compounds

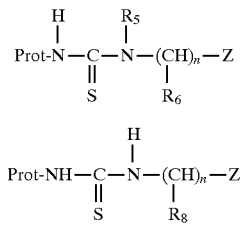

in which Prot represents a protective group, for example benzoyl, pivaloyl or tetrahydropyranyl, and $R_5$, $R_6$, n and Z are as defined above for (I), either by a basic treatment, preferably by using ammonia, sodium hydroxide or hydrazine, at a temperature ranging from room temperature to the reflux temperature of the reaction mixture, or by an acid treatment, preferably by using hydrochloric acid.

The compounds of formula (VIa) and (VIb) are prepared by reacting, according to known methods, an isothiocyanate, for a example a benzoyl isothiocyanate or a pivaloyl isothiocyanate, with the corresponding amines HNXY of formula (VIIa) and (VIIb)

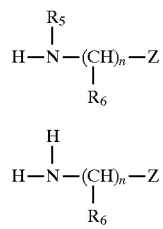

in which Y represents

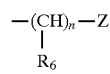

with n, $R_6$, and Z as defined for (I), and X represents hydrogen or $R_5$ as defined for (I).

When Z is a nitrogenous heterocyclic group of indole or indazole type, Route B is used, the precaution being taken of blocking the reactivity of the reactive cyclic nitrogen by substituting it by a protective group of tetrahydropyranyl type. After the alkylation of the exo nitrogen of the substituted 2-aminothiazole, the protected nitrogen of the heterocycle may be deprotected by an acid treatment, preferably with hydrochloric acid. The compound obtained may then be substituted by a nucleophilic reaction with substituted halogenated compounds, such as alkyl bromides or iodides, to obtain the compound of formula (I). Some substituted compounds may then give rise to conventional reactions such as, for example, hydrolysis of the ester or nitrile group to obtain acids or reaction of a magnesium compound with a nitrile to obtain the corresponding ketones. Activation of the acid group, either in the acid chloride form or in the activated ester form, makes it possible, by reacting with a nitrogenous base such as morpholine, to obtain the corresponding amides.

The secondary amines (VIIa) are prepared from the primary amines

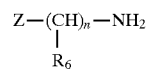

either by reacting with an aldehyde

in which $R'_5$—$CH_2$ represents $R_5$, and then reduction of the imine, for example by $NaBH_4$, preferably in ethanol or methanol at room temperature or by reacting with an acid halide or an acid anhydride in an organic solvent selected from halogenated hydrocarbons, such as dichloromethane, in the presence of a proton acceptor, preferably triethylamine. The amide resulting from this reaction is then reduced by a hydride, such as $LiAlH_4$, in organic solvents of diethyl ether type.

The two methods mentioned above are preferably used for the preparation of the compounds of formula (VIIa), in the form of pure enantiomers, from the optically pure primary amines.

Another method for the preparation of the compounds of formula (VIIa) comprises a coupling reaction of a ketone

in which Z and $R_6$ have the same meaning as for the formula (I), with an amine $R_5NH_2$, in which $R_5$ is as defined for (I), in a dehydrating medium, in order to form the corresponding imine which is then reduced conventionally by a metal hydride, preferably sodium borohydride, or by hydrogen in the presence of an appropriate catalyst. During the reaction of the primary amine with a ketone in a dehydrating medium, use is preferably made either of titanium(IV) chloride ($TiCl_4$) or of catalysis by para-toluenesulphonic acid.

The compounds of formula (I) above also comprise those in which one or a number of hydrogen or carbon atoms, for example those situated on $R_4$, in particular when it represents a methyl group, have been replaced by their radioactive isotope, for example tritium or carbon-14. Such labelled compounds are useful in research, metabolic or pharmacokinetic work or alternatively in biochemical assays as receptor ligands.

The compounds of the present invention have formed the subject of biochemical and pharmacological studies. They have highly advantageous pharmacological properties. The compounds of the invention displace, in particular at concentrations of less than 10 μM (0.01–10 μM), the binding of $^{125}$I-CRF to specific receptors present on human brain membranes (or membranes of transfected CHO cells expressing the cloned human brain receptor) and/or animal brain membranes (rat, mouse), according to the method described by De Souza E. B. (J. Neurosci., 1987, 7(1), pp. 88–100).

This is astonishing and unexpected, since compounds with a structure close to that of the compounds of the invention do not significantly displace 125I-CRF binding.

CRF is a neuropeptide which controls the activity of the hypothalamohypophysosuprarenal axis. This factor is responsible for endocrinal and behavioural responses related to stress.

Indeed, it has been shown that CRF can modulate behaviour and also some functions of the autonomous nervous system (G. F. Koob, F. E. Bloom, Fed. Proc., 1985, 44, p. 259; M. R. Brown, L. A. Fisher, Fed. Proc., 1985, 44, p. 243). More particularly, CRF induces secretion of corticotropin (ACTH), β-endorphins and other peptides derived from pro-opiomelanocortin (A. Tazi et al., Regul. Peptides, 1987, 18, p. 37; M. R. Brown et al., Regul. Peptides, 1986, 16, p. 321; C. L. Williams et al., Am. J. Physiol., 1987, G 582, p. 253).

The compounds of the invention may therefore be useful in regulating the secretion of these endogenous substances. They are more especially applied as active principles in medicines for decreasing the response to stress (behaviour, emotional states, gastrointestinal and cardiovascular disorders or disorders of the immune system) and more generally in pathologies involving CRF, for example psychiatric disorders, anxiety, depression, anorexia nervosa, disorders of sexual activity and of fertility, Alzheimer's disease or others.

The results obtained during different pharmacokinetic studies carried out with the products of the invention have shown that they are very well absorbed.

These studies have also shown that the pharmaceutical compositions prepared with the products of formula (I), which are the subject of the present invention, can be absorbed via the digestive tract without the amounts administered being such as to prohibit use in human therapeutics. The compounds of the invention are therefore useful in the preparation of pharmaceutical compositions which may be administered both parenterally and orally.

The compounds of the invention are very stable and are therefore particularly appropriate in forming the active principle of medicines.

The invention also applies to the pharmaceutical compositions containing, as active principle, a compound of formula (I) or one of its pharmaceutically acceptable salts, optionally in combination with one or a number of appropriate inert excipients.

In each dosage unit, the active principle of formula (I) is present in amounts suitable for the daily doses envisaged. In general, each dosage unit is suitably adjusted according to the dosage and the type of administration anticipated, for example tablets, gelatin capsules and the like, sachets, ampoules, syrups and the like, drops or transdermal or transmucosal patches, so that such a dosage unit contains 0.5 to 200 mg of active principle, preferably 0.5 to 800 mg having to be administered each day.

The compounds according to the invention can also be used in combination with another active principle which is useful in the desired therapy, such as, for example, anxiolytics, antidepressants or anorexics.

The compounds of formula (I) have little toxicity; their toxicity is compatible with their use as a medicine in the treatment of the above disorders and diseases.

The compounds of formula (I) can be formulated in pharmaceutical compositions for administration to mammals, including man, for the treatment of the abovesaid diseases.

The pharmaceutical compositions thus obtained are advantageously presented in various forms, such as, for example, injectable solutions or solutions to be taken orally, dragées, tablets or gelatin capsules. Pharmaceutical compositions containing at least one compound of formula (I) or one of its salts as active principle are in particular useful in the preventive or curative treatment of diseases related to stress and more generally in the treatment of all pathologies involving CRF, such as, for example: neuropsychiatric disorders, such as anxiety, panic, phobias, mood disorders, behavioural disorders, anorexia, bulimia, hyperglycaemia, retarded growth, sleep disorders and depressions of all types; Alzheimer's or Parkinson's disease; Huntington's chorea; amyotrophic lateral sclerosis; cardiovascular disorders; disorders of sexual activity and of fertility; immunodepression, immunosuppression and their associated diseases, such as inflammatory disorders, multiple infections, cancers, rheumatoid arthritis, osteoarthritis, psoriasis and diabetes; gastrointestinal disorders and inflammations which result therefrom (irritable bowel syndrome, diarrhoea); disorders of pain perception, fibromyalgias related or not related to sleep disorders, fatigue or migraine; or drug addiction or drug withdrawal symptoms.

The posology can vary widely as a function of the age, weight and state of health of the patient, of the nature and severity of the ailment and of the administration route. This posology comprises the administration of one or a number of doses of approximately 0.5 mg to 200 mg per day, preferably of approximately 0.5 to 800 mg per day.

In the pharmaceutical compositions of the present invention for oral, sublingual, subcutaneous, intramuscular, intravenous, transdermal, transmucosal, local or rectal administration, the active principle can be administered to animals and humans in unit forms of administration, mixed with conventional pharmaceutical vehicles. Appropriate unit forms of administration include forms for oral administration, such as tablets, gelatin capsules, powders, granules and solutions or suspensions to be taken orally, forms for sublingual and buccal administration, forms for subcutaneous, intramuscular, intravenous, intranasal or intraocular administration and forms for rectal administration.

If a solid composition in the form of tablets is prepared, the main active principle is mixed with a pharmaceutical vehicle such as gelatin, starch, lactose, magnesium stearate, talc, gum arabic or the like. The tablets can be coated with sucrose or other appropriate substances or they can also be treated so as to have a prolonged or delayed activity and so as to release a predetermined amount of active principle continuously.

A preparation in the form of gelatin capsules is obtained by mixing the active principle with a diluent and pouring the resulting mixture into soft or hard gelatin capsules.

A preparation in the form of a syrup or elixir can contain the active principle in combination with a sweetener, which is preferably calorie-free, and methylparaben and propylparaben as antiseptic, as well as with a flavouring and an appropriate colour.

Water-dispersible granules or powders can contain the active principle mixed with dispersants or wetting agents or with suspending agents such as polyvinylpyrrolidone, as well as with sweeteners or taste correctors.

Rectal administration is effected using suppositories which are prepared with binders melting at the rectal temperature, for example cocoa butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol or butylene glycol.

For transmucosal administration, the active principle can be formulated in the presence of a promoter, such as a bile salt, or of a hydrophilic polymer, such as, for example, hydroxypropylcellulose, hydroxypropylmethylcellulose, hydroxyethylcellulose, ethylcellulose, carboxymethylcellulose, dextran, polyvinylpyrrolidone, pectins, starches, gelatin, casein, acrylic acids, acrylic esters and their copolymers, vinyl polymers or copolymers, vinyl alcohols, alkoxypolymers, polymers of poly(ethylene oxide), polyethers or their mixture.

The active principle can also be formulated in the form of microcapsules, optionally with one or a number of vehicles or additives.

The active principle can also be presented in the form of a complex with a cyclodextrin, for example α-, β- or γ-cyclodextrin, 2-hydroxypropyl-β-cyclodextrin or methyl-β-cyclodextrin.

The following EXAMPLES, given without implied limitation, illustrate the invention.

The methods for the synthesis of the different intermediates which make it possible to obtain the compounds of the invention are described in the different PREPARATIONS. These intermediates are all obtained according to methods which are well known to the person skilled in the art.

The melting points were measured according to the Micro-Köfler technique and are expressed in degrees Celsius.

The proton nucleic magnetic resonance spectra ($^1$H NMR) of the compounds of formula (I) were recorded, as the case may be, at 200 MHz or at 100 MHz. The chemical shifts are given in ppm and the coupling constants in Hertz.

The compounds of the invention have an elemental analysis in accordance with theory.

The compounds of the invention described in TABLES I to IV also have NMR spectra in accordance with their structure.

PREPARATIONS

PREPARATION OF THE KETONES OF FORMULA II

PREPARATION I

2-Bromo-1-(2,4-dichlorophenyl)propan-1-one (Compound 1)

17.4 g of tetra-butylammonium tribromide are added at room temperature to 7 g of 1-(2,4-dichlorophenyl)propan-1-one in solution in a mixture of 420 ml of methylene chloride and 140 ml of methanol. After 24 hours, the reaction mixture is concentrated under vacuum. The residue is taken up in water and extracted with ethyl acetate, the organic phase is dried with sodium sulphate and evaporated under vacuum and the residue is then purified on a column of silica gel with a 20/1 (v/v) mixture of cyclohexane and ethyl acetate as eluent, to obtain an oil.

By using the appropriate ketones, the following compounds can also be obtained in the same way:

2-bromo-1-(4-chloro-2-methoxyphenyl)propan-1-one (Compound 2)

2-bromo-1-(4-chloro-2-methoxyphenyl)propan-1-one (Compound 3)

2-bromo-1-(2-bromo-4-methoxyphenyl)propan-1-one (Compound 4)

2-bromo-1-(2-chloro-4-methoxyphenyl)propan-1-one (Compound 5)

2-bromo-1-(2-chloro-4-methylphenyl)propan-1-one (Compound 6)

2-bromo-1-(4-chloro-2-methylphenyl)propan-1-one (Compound 7)

PREPARATION II

2-Bromo-1-(2-chloro-4-trifluoromethylphenyl)-propan-1-one (Compound 8)

Stage 1: A suspension of 10 g of 2-chloro-4-trifluoromethylaniline in 18 g of 95% sulphuric acid and 65 ml of water is slowly added at 15° C. to a solution of 3.57 g of sodium nitrite in 7 ml of water. The reaction mixture is stirred at 40°–45° C. for 2 hours and then carefully poured onto the following mixture maintained at 95° C.: 10.77 g of sodium cyanide, 0.51 g of copper cyanide, 25.8 g of sodium hydrogencarbonate and 0.46 g of nickel sulphate hydrate in 30 ml of water. The reaction mixture is stirred at 100° C. for 1 hour and then, after cooling, 30 ml of a saturated aqueous sodium hydrogencarbonate solution are added and extraction is carried out with dichloromethane. The extract is filtered through celite and then successively washed with water, with salted water, dried over sodium sulphate and evaporated to dryness. The residue is purified on a column of silica gel, eluent: 20/1 (v/v) cyclohexane/ethyl acetate, and 3.55 g of 2-chloro-4-trifluoromethylbenzonitrile are obtained in the form of a brown oil. $^1$H NMR (CDCl$_3$): 7.4 to 7.8 (m, 3H).

Stage 2: A solution of 3.6 g of the product prepared above in 50 ml of benzene is stirred at 20° C. and 11.7 ml of a 3M solution of ethylmagnesium bromide in diethyl ether are added. The reaction mixture is stirred at reflux for 2 hours, then cooled to 0° C. and 17.5 ml of 6N hydrochloric acid are added slowly. After stirring at reflux for 3 hours and then cooling, the reaction mixture is extracted with diethyl ether. The extract is washed with salted water, dried over sodium sulphate and evaporated to dryness. The evaporation residue is purified by chromatography on a column of silica gel, eluent: 20/1 (v/v) cyclohexane/ethyl acetate, and 83.2 g of 1-(2-chloro-4-trifluoromethylphenyl)propane-1-one are obtained. $^1$H NMR (CDCl$_3$): 1.2 (m, 3H), 2.9 (m, 2H), 7.45 to 7.62 (m, 3H).

Stage 3: 7.65 g of tetrabutylammonium tribromide are added to a solution of 3.5 g of the product prepared above in 150 ml of dichloromethane. The reaction mixture is stirred at 35° C. for 4 hours 30 and then, after cooling, is washed 3 times with water to neutrality. The organic phase is evaporated and the residue is taken up in diethyl ether. The ethereal phase is washed successively with water and with salted water, then dried over sodium sulphate and evaporated to dryness to provide 4.6 g of 2-bromo-1-(2-chloro-4-trifluoromethylphenyl)-propan-1-one. $^1$H NMR (CDCl$_3$): 1.9 (d, 3H), 5.2 (q, 1H), 7.5 to 7.7 (m, 3H).

PREPARATION OF THE AMINES

PREPARATION III

N-Naphth-1-yl-N-propylamine (Compound 9)

Stage 1: 4.0 g of 1-naphthylamine are dissolved in 40 ml of tetrahydrofuran, 2.6 g of propanoyl chloride are then added dropwise and the reaction mixture is left stirring for 2 hours and then evaporated to dryness. The residue obtained is taken up in dichloromethane and washed with an aqueous sodium chloride solution. The organic phase is dried over sodium sulphate and evaporated to dryness to obtain 5.5 g of white crystals of N-propionyl-1-naphthylamine, melting at 127° C. $^1$H NMR (CDCl$_3$): 1.28 (t, J=7.3, 3H, —CH$_2$—CH$_3$), 2.51 (q, J=7.3, 2H, —CH$_2$—CH$_3$), 7.30–7.50 (m, 3H, H$_2$, H$_3$ and H$_8$), 7.55–7.85 (m, 4H, H$_6$, H$_7$, H$_4$ and H$_5$).

Stage 2: 5.5 g of the amide prepared above are dissolved in 50 ml of anhydrous tetrahydrofuran in a three-necked flask equipped with a dropping funnel and maintained under argon, the reaction mixture is then heated to 50° C. and 42 ml of 2M borane-dimethyl sulphide are added dropwise and the reaction mixture is left under reflux for 3 hours and at room temperature overnight. The mixture is cooled in an ice bath; 100 ml of 6N hydrochloric acid are then added and the mixture is then heated at reflux for 3 hours. The tetrahydrofuran is evaporated and then, successively, the residue is basified and extracted with ethyl acetate and the organic phase is dried over sodium sulphate and evaporated to dryness to obtain 3.9 g of a colourless oil. $^1$H NMR (CDCl$_3$): 1.10 (t, J=7.3, 3H, CH$_2$—CH$_3$), 2.51 (sex, J=7.3, 2H, —CH$_2$—CH$_3$), 3.26 (t, J=7.3, 2H, —CH$_2$—CH$_2$—CH$_3$), 4.33 (m, 1H, NH); 6.61 (d, J=7.3, 1H, H$_2$), 7.23 (d, J=8.4, 1H, H$_3$), 7.34 (d, J=1H, H$_8$), 7.40–7.50 (m, 2H, H$_6$ and H$_7$), 7.75–7.90 (m, 2H, H$_4$ and H$_5$)

PREPARATION IV

N-Propyl-N-quinol-5-ylamine (Compound 10)

5 g of 5-aminoquinoline, 3 ml of propionaldehyde and 4.7 g of para-thiocresol are dissolved in 100 ml of ethanol in a 250 ml round-bottomed flask. The reaction mixture is heated at reflux for 2 hours and then evaporated to dryness. The residue is dissolved in 100 ml of ethanol and cooled in an ice bath and then 6.5 g of sodium borohydride are added portionwise. When addition is complete, the reaction mixture is heated at reflux for 2 hours and then, successively, 30 ml of water are added, the mixture is basified with 20 ml of concentrated sodium hydroxide and stirred for 15 minutes and the organic solvents are evaporated. Extraction is carried out with dichloromethane and the organic phase is washed with water and then dried over sodium sulphate. The organic phase is evaporated to dryness and the residue is purified on a column of silica gel, eluent: ethyl acetate, to obtain 4 g of an oil which crystallizes. $^1$H NMR (CDCl$_3$): 1.05 (t, J=3H, —CH$_3$), 1.82–1.71 (m, 2H, —CH$_2$—CH$_3$), 3.15–3.26 (m, 2H, —NH—CH$_2$—), 4.37 (sl, 1H, —NH—), 6.61 (dd, J=1.0, J=8.6, 1H, H$_4$), 7.26 (dd, J=4.2, J=8.6, 1H, H$_6$), 7.44–7.59 (m, 2H, H$_3$, H$_2$), 8.12 (dd, J=0.95, J=8.6, 1H, H$_8$), 8.84 (dd, J=1.5, J=4.2, H$_2$).

By carrying out the preparation in the same way, N-propyl-N-quinol-6-ylamine (Compound 11) is prepared.

PREPARATION V

N-(1-Naphth-1-yl-2-methoxyethyl)-N-propylamine (Compound 12)

Stage 1: The magnesium compound of 1-bromonaphthalene is prepared from 25 g of 1-bromonaphthalene and 3.5 g of magnesium in 50 ml of diethyl ether, the solution is then cooled on ice and 9 ml of methoxyacetonitrile, in solution in 20 ml of diethyl ether, are added dropwise. The reaction mixture is then stirred for 2 hours at room temperature and then cooled to 0° C. 100 ml of a saturated ammonium chloride solution are then added and extraction is carried out with diethyl ether. The organic phase is successively washed with a saturated sodium chloride solution, dried over sodium sulphate and evaporated to dryness to provide 29 g of oily residue of methoxymethyl 1-napthyl ketone.

Stage 2: The ketone obtained above is dissolved in 350 ml of dichloromethane and then 50 ml of propylamine and then, at 5° C. and dropwise, 120 ml of a 1M solution of TiCl$_4$ in dichloromethane are added. The reaction mixture is left stirring at room temperature for 20 hours and then 200 ml of methanol are added. The solution is cooled in an ice bath, 4.6 g of NaBH$_4$ are then added portionwise and the mixture is allowed to gradually return to room temperature. After stirring for 3 hours, the reaction mixture is filtered through celite and the filtrate is evaporated to dryness. The residue is taken up in dichloromethane. The solution is washed with 1N hydrochloric acid. The combined aqueous phases are basified and the product is extracted with 4 times 200 ml of dichloromethane to provide 5.1 g of the expected amine. $^1$H NMR (DMSO): 0.77 (m, 3H), 1.27–1.44 (m, 2H), 2.00–2.47 (m, 2H), 3.25 (8, 3H), 3.28–3.49 (m, 2H), 4.64–4.70 (m, 1H), 7.19–8.29 (m, 8H).

By carrying out the preparation as shown for PREPARATION V above, N-(1-naphth-2-yl-2-methoxyethyl)-N-propylamine (Compound 13) is prepared.

PREPARATION VI

5-Amino-6-methoxyquinoline (Compound 14)

Stage 1: 4.0 g of 6-methoxyguinoline are dissolved in 70 ml of acetic acid, the solution is then cooled to 0° C. and 5.5 g of KNO$_3$ are added. The reaction mixture is stirred at 0° C. for 1 hour and then basified with 10N sodium hydroxide. The yellow precipitate obtained is filtered off and washed copiously with water to obtain 4.9 g of a yellow powder of 6-methoxy-5-nitroquinoline. $^1$H NMR (CDCl$_3$): 4.07 (s, 3H —OCH$_3$), 7.48–7.54 (m, 1H, H$_3$), 7.58 (d, J=9.5, 1H, H$_7$), 8.04 (d, J=8.8, 1H, H$_4$), 8.25 (d, J=9.5, 1H, H$_8$), 8.86 (dd, J=1.5, J=4.2, 1H, H$_2$).

Stage 2: 4.9 g of 6-methoxy-5-nitroquinoline are dissolved in 100 ml of acetic acid and 60 ml of 37% hydrochloric acid, 51 g of SnCl$_2$ are then added and the reaction mixture is heated at reflux for 3 hours and then at room temperature for 12 hours. The reaction mixture is then evaporated to dryness and the residue is taken up in water and basified with a saturated NaHCO$_3$ solution. Extraction is carried out with ethyl acetate and the organic phase is dried over sodium sulphate and then evaporated to dryness to obtain 2.9 g of a yellow powder of 6-methoxy-5-quinolylamine. $^1$H NMR (CDCl$_3$): 4.00 (s, 3H, —OCH$_3$), 4.28 (m, 2H, —NH$_2$), 7.28–7.34 (m, 1H, H$_3$), 7.44 (d, J=9.1, 1H, H$_7$), 7.60 (d, J=9.1, 1 H, H$_4$), 8.14 (dd, J=0.7, J=9.5, 1H, H$_8$), 8.78 (dd, J=1.8, J=4.2, 1H, H$_2$).

By carrying out the preparation as shown for PREPARATION VI above, 5-amino-6-chloro-2-methylquinoline (Compound 15) is prepared.

PREPARATION VII

2-Amino-1-methoxynaphthalene (Compound 16)

Stage 1: 10 g of 1-methoxynaphthalene are dissolved in 100 ml of acetic anhydride and then 2.6 ml of concentrated HNO$_3$, dissolved in 15 ml of acetic anhydride, are added dropwise. The reaction mixture is stirred for 30 minutes at room temperature and is then basified with a saturated NaHCO$_3$ solution. The brown precipitate formed is filtered off and taken up in ethyl acetate and the organic phase is then successively washed copiously with a saturated NaCl solution, dried over sodium sulphate and evaporated to dryness. The residue obtained is purified by chromatography on a column of silica gel eluted with a 5/95 (v/v) ethyl acetate/hexane mixture for the first isomer and then 10/90

(v/v) ethyl acetate/hexane for the second isomer. 2.45 g of the desired product are thus obtained (Y=19%). $^1$H NMR (CDCl$_3$): 4.15 (s, 3H, —OCH$_3$), 7.64–7.71 (m, 5H, H$_3$, H$_4$, H$_6$, H$_7$, H$_8$), 8.30–8.34 (m, 1H, H$_5$).

Stage 2: 2.45 g of the product obtained above are dissolved in 50 ml of acetic acid and 25 ml of concentrated HCl. 8.2 g of SnCl$_2$·H$_2$O are added and the reaction mixture is heated at reflux for 3 hours and then stirred for 12 hours at room temperature. The precipitate is filtered off, then taken up in a saturated NaHCO$_3$ solution and extracted with ethyl acetate. The filtrate is evaporated and the residue is basified with a saturated NaHCO$_3$ solution and then extracted with ethyl acetate. The two ethyl acetate solutions are combined and then dried and evaporated to dryness. The residue obtained is purified by chromatography on a column of silica gel eluted with a 50/50 (v/v) ethyl acetate/hexane mixture. 1.75 g of the desired product are thus obtained in the form of an oil (Y=84%). $^1$H NMR (CDCl$_3$): 3.91 (s, 3H, —OCH$_3$), 3.98 (m, 2H, —NH$_2$), 7.03 (d, J=8.8, 1H, H$_3$), 7.27 (t, J=7.7, 1H, H$_7$), 7.47–7.52 (m, 2H, H$_4$, H$_6$), 7.73 (d, J=8.0, 1H, H$_8$), 7.94 (d, J=8.4, 1H, H$_5$).

By carrying out the preparation as shown for PREPARATION VII above, the following are prepared:

1-amino-4-methoxynaphthalene (Compound 17)

5-amino-6-methoxyquinoxaline (Compound 18), SnCl$_2$ being replaced by TiCl$_3$ 1-amino-2-ethoxynaphthalene (Compound 19)

1-amino-2-propoxynaphthalene (Compound 20)

1-amino-2,3-dimethylnaphthalene (Compound 21)

1-amino-2-methoxy-6-bromonaphthalene (Compound 22)

1-amino-2,6-dimethylnaphthalene (Compound 23)

1-amino-2-(2-methoxyethoxy)naphthalene (Compound 24)

PREPARATION VIII

1-Amino-2-methoxy-4-ethylnaphthalene (Compound 25)

Stage 1: 7.5 g of 2-methoxynaphthalene are dissolved in 80 ml of acetic acid. The solution is cooled to 0° C., 2.2 ml of concentrated HNO$_3$ are then added and the mixture is stirred for 1 hour at 0° C. The reaction mixture is left for 12 hours at room temperature. The yellow precipitate formed is filtered off and then washed with water. The filtrate is taken up in water and then extracted with ethyl acetate and 4 g of the expected product are obtained in the form of a yellow powder (Y=42%). $^1$H NMR (CDCl$_3$): 4.02 (s, 3H, —OCH$_3$), 7.33 (d, J=9.1, 1H, H$_3$), 7.45 (t, J=7.3, 1H, H$_7$), 7.70–7.55 (m, 2H, H$_6$, H$_8$), 7.83 (d, J=7.7, 1H, H$_5$), 7.95 (d, J=9.1, 1H, H$_4$).

Stage 2: 4 g of the product obtained above are dissolved in 80 ml of anhydrous THF at 0° C. and then a solution of a magnesium compound (0.96 g of magnesium in 50 ml of anhydrous THF, to which are added 2.9 ml of ethyl bromide and a few crystals of iodine) is added. The reaction mixture is stirred for 1 minute at 0° C. and then 50 ml of a saturated NH$_4$Cl solution are added. The extraction is carried out with ethyl acetate and the organic phase is dried over sodium sulphate and then evaporated to dryness. The residue is taken up into 50 ml of anhydrous THF and then 5.3 g of 2,3-dicyano-5,6-dichloro-1,4-benzoquinone are added. The reaction mixture is heated at reflux for 4 hours and then evaporated to dryness. The residue obtained is purified by chromatography on a column of silica gel eluted with a 25/75 (v/v) ethyl acetate/hexane mixture. 1.8 g of the expected product are obtained in the form of a white powder (Y=40%), M.p.=80° C., $^1$H NMR (CDCl$_3$); 1.41 (t, J=7.5, 3H, —CH$_2$—CH$_3$), (q, J=7.5, 2H, —CH$_2$—CH$_3$), 4.04 (s, 3H, —OCH$_3$), 7.20 (s, 1H, H$_3$), 7.46–8.01 (m, 4H, H$_5$, H$_6$, H$_7$, H$_8$).

Stage 3: 1.8 g of the product obtained above are dissolved in 40 ml of acetic acid and 20 ml of 37% HCl. 5.3 g of SnCl$_2$·H$_2$O are added and the reaction mixture is heated at reflux for 12 hours. The precipitate obtained is filtered off and then taken up in water and basified with a saturated NaHCO$_3$ solution. Extraction is carried out with ethyl acetate, the organic phase is dried over sodium sulphate and then evaporated to dryness and 1.4 g of the expected product are obtained in the form of a yellow powder (Y=90%). $^1$H NMR (CDCl$_3$): 1.37 (t, J=7.5, 3H, —CH$_2$—CH$_3$), 3.06 (q, J=7.5, 2H, —CH$_2$—CH$_3$), 3.98 (s, 3H, OCH$_3$), 7.13 (S, 1H, H$_3$), 7.34–7.50 (n, 2H, H$_6$, H$_7$), 7.82 (d, J=8.2, 1H, H$_5$), 7.88 (d, J=8.2, 1H, H$_8$)

By carrying out the preparation as shown for PREPARATION VIII above, 1-amino-2-methoxy-4-isopropyl-naphthalene (Compound 26) is prepared.

PREPARATION IX

5-Amino-6-methoxyisoquinoline (Compound 27)

Stage 1: 9.5 g of 4-methoxybenzaldehyde and 7.8 g of aminoacetaldehyde dimethyl acetal, diluted in 50 ml of benzene, are introduced into an assembly equipped with a Dean and Stark apparatus. The reaction mixture is heated to reflux for 12 hours. The solution is evaporated to dryness and then taken up twice in benzene before being evaporated to dryness. The oil obtained is dissolved in anhydrous tetrahydrofuran and is maintained at –10° C., one equivalent of ethyl chloroformate is then added with rapid stirring and the reaction mixture is left stirring for a further 5 minutes and the ice bath is removed (appearance of a yellow precipitate). 10.5 ml of trimethyl phosphite are added at room temperature. Stirring is maintained for 15 hours and the reaction mixture is evaporated to dryness. In order to remove all traces of trimethyl phosphite, the oil is taken up in toluene and evaporated to dryness; this operation is carried out twice. The oil is dissolved in anhydrous dichloromethane; 6 equivalents of titanium tetrachloride are added and the solution is heated at reflux for 36 hours under anhydrous conditions. The solution is cooled and one equivalent of an aqueous sodium hydroxide solution is added, with stirring, to neutralization. TiO$_2$ precipitates in the form of a white solid. Filtration is carried out and the solution is extracted with a 3N hydrochloric acid solution, the aqueous phase is washed with dichloromethane, basified with a strong base and extracted with dichloromethane and the organic phase is dried over sodium sulphate and evaporated to dryness to obtain 6.2 g of a light-orange oil of 6-methoxyisoquinoline. $^1$H NMR (CDCl$_3$): 3.95 (s, 3H, —OCH$_3$), 7.06 (d, J=2.2, 1H, H$_5$), 7.21 (dd, J=8.7, J=2.2, 1H, H$_7$), 7.55 (d, J=5.8, 1H, H$_4$), 7.85 (d, J=8.7, 1H, H$_8$), 8.44 (d, J=5.8, 1H, H$_3$), 9.11 (s, 1H, H$_1$).

Stage 2: 1.2 g of potassium nitrate are added to a solution of 1.0 g of 6-methoxyisoquinoline, prepared above, in 20 ml of concentrated sulphuric acid, the whole mixture being maintained in an ice bath. After stirring for 1 hour, distilled water is added and then, successively, the mixture is basified and the precipitate is filtered off and dried to obtain 1.2 g of yellow crystals of 6-methoxy-5-nitroisoquinoline. 1H NMR (CDCl$_3$): 4.08 (s, 3H, —OCH$_3$), 7.44 (d, J=9.1, 1H, H$_7$), 7.52 (d, J=6.2, 1H, H$_4$), 8.12 (d, J=9.1, 1H, H$_8$), 8.57 (d, J=6.2, 1H, H$_3$), 9.20 (d, J=0.7, 1H, H$_1$).

Stage 3: 0.9 g of the substituted nitro compound prepared above is dissolved in a solution of 40 ml of acetic acid and 22 ml of concentrated hydrochloric acid, 10.2 g of tin chloride are then added and the reaction mixture is heated at reflux for 3 hours and then at room temperature for 12 hours. The mixture is basified and extracted with dichloromethane and the organic phase is dried and evaporated to dryness to obtain 0.7 g of yellow crystals of the expected amine. $^1$H NMR (CDCl$_3$): 3.96 (s, 3H, —OCH$_3$), 4.26 (broad s exchangeable with D$_2$O, 2H, —NH$_2$), 7.25 (d, J=9.1, 1H, H$_7$), 7.40 (d, J=9.1, 1H, H$_8$), 7.48 (d, J=5.8, 1H, H$_4$), 8.35 (d, J=6.2, 1H, H$_3$), 9.07 (s, 1H, H$_1$).

PREPARATION X

5-Amino-6-methylisoquinoline (Compound 28)

By carrying out the preparation according to Stages 1 and 2 of PREPARATION IX above and by using 4-methylbenzaldehyde as starting reactant, 6-methyl-5-nitroisoquinoline is prepared. 4.0 g of 6-methyl-5-nitroisoquinoline are dissolved in a solution of 80 ml of acetic acid and 40 ml of concentrated hydrochloric acid, 40.0 g of tin chloride are then added and the reaction mixture is heated at reflux for 3 hours and then left for 12 hours at room temperature. The crystals formed are filtered off, taken up in water and basified with 10N sodium hydroxide. The extraction is carried out with dichloromethane and the organic phase is dried and evaporated to dryness to obtain 0.52 g of yellow crystals. $^1$H NMR (CDCl$_3$): 2.37 (s, 3H, —CH$_3$), 4.18 (broad s exchangeable with D$_2$O, 2H, —NH$_2$), 7.29 (d, J=8.8, 1H, H$_7$), 7.44 (d, J=8.8, 1H, H$_4$), 7.53 (d, J=6.2, 1H, H$_8$), 8.49 (d, J=5.8, 1H, H$_3$), 9.13 (s, 1H, H$_1$).

PREPARATION XI

5-Amino-1-tetrahydropyran-2-ylindole (Compound 29)

Stage 1: 6.3 g of 55% NaH are added, at 0° C., under an argon atmosphere, to 20 g of 5-nitroindole in solution in 200 ml of dimethylformamide. After stirring for 15 minutes at 0° C., 27.1 g of tetrahydropyranyl chloride are added to the reaction mixture. After stirring for 24 hours at room temperature, the reaction mixture is poured onto 1200 ml of ice-cold water and extracted with ethyl acetate. The combined organic phases are dried over sodium sulphate and evaporated to dryness. The residue is purified by chromatography on a column of silica gel eluted with a 4/1 (v/v) cyclohexane/ethyl acetate mixture, to provide 19 g of 5-nitro-1-tetrahydropyran-2-ylindole. $^1$H NMR (DMSO): 1.34–2.12 (m, 6H), 3.67–4.48 (m, 2H), 5.70 (dd, J=2.0, 10.2, 1H), 6.75 (d, J=3.4, 1H), 7.72–7.76 (m, 2H), 8.02 (dd, J=2.2, 9.2, 1H), 8.54 (d, J=2.2, 1H).

Stage 2: 17 g of 5-nitro-1-tetrahydropyran-2-ylindole are dissolved in 170 ml of methanol and then 3 g of 10% Pd-on-charcoal and then, portionwise at 0° C., 20.6 g of ammonium formate are added. After stirring for 1 hour 30 at room temperature, the reaction mixture is filtered and the filtrate is evaporated to dryness. The residue is taken up in 300 ml of ethyl acetate. The solution is washed with 800 ml of water, dried over sodium sulphate and evaporated to dryness. 14.2 g of 5-amino-1-tetrahydropyran-2-ylindole are obtained in the solid form. A sample is purified by chromatography on a column of silica gel eluted with a 3/1 (v/v) cyclohexane/ethyl acetate mixture, to provide (Compound 29). $^1$H NMR (DMSO): 1.30–2.20 (m, 6H), 3.59–3.93 (m, 2H), 4.72 (m, 2H), 5.41 (dd, J=1.8, 12.0, 1H), 6.16 (d, J=3.2, 1H), 6.52 (dd, J=2.0, 8.6, 1H), 6.66 (d, J=2.0, 1H), 7.20 (d, J=8.6, 1H), 7.27 (d, J=3.2, 1H).

PREPARATION OF THE THIOUREAS

PREPARATION XII

N-Naphth-1-yl-N-propylthiourea (Compound 30)

3.9 g of benzoyl chloride and 2.1 g of ammonium thiocyanate are introduced into anhydrous acetone in a three-necked flask under argon and maintained between 0° and 5° C., the reaction mixture is left stirring for 15 minutes and then 3.9 g of N-naphth-1-yl-N-propylamine, dissolved in acetone, are added dropwise. The reaction mixture is then heated at reflux for 1 hour and evaporated to dryness and the residue is taken up in concentrated hydrochloric acid, heated at reflux for 3 hours and allowed to return to room temperature. The organic products are extracted with diethyl ether and then successively basification is carried out with 33% sodium hydroxide, extraction is carried out with ethyl acetate, the organic phase is evaporated to dryness and the residue is purified on a column of silica gel eluted with a 75/25 (v/v) hexane/ethyl acetate mixture, to obtain 3.2 g of white crystals melting at 170°–171° C. 1H NMR (CDCl$_3$): 0.86 (t, J=7.3, 3H, —CH$_2$—CH$_3$), 1.68 (m, 2H, —CH$_2$—CH$_3$), 3.72 (m, 2H, —CH$_2$—CH$_2$—CH$_3$), 5.58 (m, 2H, —NH$_2$), 7.37 (d, J=7.3, 1H, H$_2$), 7.23 (m, 2H, H$_3$ and H$_8$), 7.75–7.80 (m, 2H, H$_6$ and H$_7$), 7.85–7.95 (m, 2H, H$_4$ and H$_5$).

PREPARATION XIII

N-Propyl-N-quinol-5-ylthiourea (Compound 31)

1.54 g of ammonium thiocyanate are dissolved in 50 ml of acetone under argon in a three-necked flask equipped with a dropping funnel, 2.5 ml of benzoyl chloride are then added dropwise and the formation of a white precipitate is observed. Once the addition is complete, heating is carried out at 60° C. (gentle reflux) for 15 minutes, the reaction mixture is then allowed to return to room temperature and 3.6 g of N-propyl-N-quinol-5-ylamine (Compound 10), dissolved in 10 ml of acetone, are added dropwise. The reaction mixture is heated at reflux for 3 hours and then, successively, evaporation is carried out to dryness, water is added, extraction is carried out with dichloromethane and the organic phase is evaporated to dryness.

The compound thus obtained is deprotected by treatment with 30 ml of a 15% solution of ammonia in ethanol at reflux overnight and then, successively, the solvent is evaporated, the residue is extracted with dichloromethane and the organic phase is dried over sodium sulphate and evaporated to dryness. The residue is purified on a column of silica gel, eluent: 6/4 (v/v) ethyl acetate/hexane. 1.5 g of a yellow powder of the expected thiourea are isolated. $^1$H NMR (CDCl$_3$): 0.91 (t, J=3H, —CH$_3$), 1.64–1.79 (m, 2H, —CH$_2$—CH$_3$), 4.19–4.24 (m, 2H, >N—CH$_2$—), 5.73 (sl, 2H, —NH$_2$), 7.47 (dd, J=4.2, J=8.3, 1H, H$_4$), 7.55 (dd, J=2.3, J=8.9, 1H, H$_7$), 7.71 (d, J=2.3, 1H, H$_5$), 8.14–8.22 (m, 2H, H$_3$, H$_8$), 8.97 (dd, J=1.7, J=4.2, H$_2$).

By carrying out the preparation according to PREPARATION XIII above, N-propyl-N-quinol-6-ylthiourea (Compound 32) is prepared.

PREPARATION XIV

N-(1-Naphth-1-yl-2-methoxyethyl)-N-propylthiourea (Compound 33)

Stage 1: 1.68 g of ammonium thiocyanate are suspended in 65 ml of acetone. The reaction mixture is cooled in ice and 2.5 ml of benzoyl chloride, in solution in 5 ml of acetone, are added. After stirring for 15 minutes at 5° C., 5.1 g of N-(1-naphth-1-yl-2-methoxyethyl)-N-propylamine, in solution in 60 ml of acetone, are added dropwise. After stirring for 3 hours between 5 and 25° C., the acetone is evaporated to dryness, the residue is taken up in dichloromethane and the solution is washed with water. The organic phase is then dried over sodium sulphate and evaporated to dryness. The residue is purified by chromatography on silica gel eluted with a 9/1 (v/v) cyclohexane/ethyl acetate mixture, to provide 5.50 g of N'-benzoyl-N-(1-naphth-1-yl-2-methoxyethyl)-N-propylamine.

Stage 2: 5.50 g of the compound prepared above are dissolved in 100 ml of methanol and then 0.60 ml of hydrazine hydrate is added. The reaction mixture is left stirring at room temperature for 20 hours. The methanol is evaporated and the residue is purified by chromatography on silica gel eluted with a 3/1 (v/v) cyclohexane/ethyl acetate mixture, to provide 2.19 g of thiourea in the form of a yellow solid.

PREPARATION XV

N-[6-Methoxyquinol-5-yl]thiourea (Compound 34)

1.7 g or ammonium thiocyanate are dissolved in 50 ml of acetone, 2.5 ml of benzoyl chloride are then added and the reaction mixture is heated at reflux for 15 minutes. 2.9 g of amine (Compound 14), dissolved in 20 ml of acetone, are added and the reaction mixture is then heated to reflux for 30 minutes. Evaporation is carried out to dryness and the residue is taken up in water and then extracted with ethyl acetate. The residue is deprotected by treatment with 5 ml of 33% ammonia in 10 ml of ethanol at reflux for 2 hours. The precipitate formed is separated off by filtration, the filtrate is evaporated and the residue is triturated with a 75/25 (v/v) ethyl acetate/hexane mixture, to obtain 3.5 g of white powder. $^1$H NMR (CDCl$_3$): 3.93 (s, 3H, —OCH$_3$), 7.50–7.53 (m, 1H, H$_3$), 7.70 (d, 1H, J=9.5, 1H, H$_7$), 8.00 (d, J=9.5, 1H, H$_4$), 8.08 (d, 1H, H$_8$), 8.75 (d, J=2.5, 1H, H$_2$).

PREPARATION XVI

N-[6-Methoxyisoquinol-5-yl]thiourea (Compound 35)

The thiourea is prepared under the normal conditions, using 3.8 g of the amine obtained above (Compound 27), 1.8 g of ammonium thiocyanate and 4.8 ml of benzoyl chloride in anhydrous acetone. Deprotection is carried out in basic medium in 33% ammonia and makes it possible to obtain, after purification by chromatography on a column of silica gel eluted with ethyl acetate, 3.24 g of white crystals melting at 186° C. $^1$H NMR (DMSO): 3.96 (s, 3H, —OCH$_3$), 7.55 (m, 4H, where (d, J=6.6, 1H, H$_4$) is recognized at 7.50 and (d, J=9.1, 1H, H$_7$) is recognized at 7.61, 2H, —NH$_2$), 8.12 (d, 9.1, 1H, H$_8$), 8.42 (d, J=5.8, 1H, H$_3$), 9.20 (m, 2H, where (s, 1H, H$_1$) is recognized at 9.19, 1H, —NH).

PREPARATION XVII

N-[6-Methylisoquinol-5-yl]thiourea (Compound 36)

1.7 g of ammonium thiocyanate are dissolved in 30 ml of acetone, 2.6 ml of benzoyl chloride are then added and the reaction mixture is heated at reflux for 15 minutes. 2.7 g of 6-methyl-5-isoquinolylamine (Compound 28), dissolved in 20 ml of acetone, are added. The reaction mixture is heated for 30 minutes and then evaporated to dryness. The residue is taken up in water and the remaining precipitate is filtered off. The compound thus obtained is deprotected with 10 ml of a 30% ammonia solution and 20 ml of ethanol at reflux for 2 hours. Evaporation is carried out to dryness and the residue is triturated in a 75/25 (v/v) ethyl acetate/hexane mixture, to obtain 3.5 g of a white powder. $^1$H NMR (CDCl$_3$): 2.38 (s, 3H, —CH$_3$), 3.36 (s, 2H, —NH$_2$), 6.58 (s, 1H, —NH—), 7.47–7.60 (m, 2H, H$_7$, H$_4$), 7.98 (m, 1H, H$_8$), 8.50 (m, 1H, H$_3$), 9.26 (s, 1H, H$_1$).

By carrying out the preparations according to PREPARATIONS I to XVII above, using the appropriate starting materials, the intermediates are prepared which make possible the synthesis of the compounds (I) according to the invention.

EXAMPLE 1

4-(2-Chloro-4-methoxyphenyl)-5-methyl-2-(N-naphth-1-yl-N-propylamino)thiazole.

(I): R$_1$=Cl; R$_2$=OCH$_3$; R$_3$=H; R$_4$=CH$_3$; R$_5$=—CH$_2$CH$_2$CH$_3$; n=0;

Z = 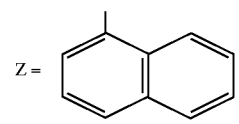

A solution containing 0.5 g of N-naphth-1-yl-N-propylthiourea and 0.5 g of 2-bromo-1-(2-chloro-4-methoxyphenyl)propan-1-one in 15 ml of methanol is heated at reflux for 6 hours. The reaction mixture is then evaporated to dryness and then, successively, the residue is taken up in water, basified with 33% sodium hydroxide and extracted with ethyl acetate and the organic phase is dried over sodium sulphate, filtered and concentrated under vacuum. The residue is then purified on a column of silica gel eluted with ethyl acetate, to provide 0.56 g of a yellow oil. $^1$H NMR (CDCl$_3$): 0.97 (t, J=7.7, 3H, —CH$_2$—CH$_3$), 1.73 (sex, 2H, —CH$_2$—CH$_3$), 2.04 (s, 3H, —CH$_3$), 3.82 (s, 3H, —OCH$_3$), 3.90 (m, 2H, —CH$_2$—CH$_2$—CH$_3$), 6.89 (dd, J=1.8, J=8.0, 1H, H$_{5arom}$) 7.02 (d, J=1.8, 1H, H$_{3arom}$), 7.50–7.70 (m, 4H, H$_2$, H$_3$, H$_8$ and H$_{6arom}$), 7.85–8.10 (m, H, H$_6$, H$_7$, H$_4$ and H$_5$).

EXAMPLE 2

4-(4-Chloro-2-methoxyphenyl)-5-methyl-2-(N-propyl-N-quinol-5-ylamino)thiazole hydrochloride.

(I): R$_1$=OCH$_3$; R$_2$=Cl; R$_3$=H; R$_4$=CH$_3$; R$_5$=—CH$_2$CH$_2$CH$_3$; n=0;

Z = 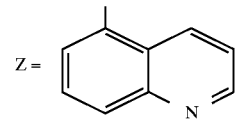

A solution containing 0.4 g of N-propyl-N-quinol-5-ylthiourea (Compound 31) and 0.5 g of 2-bromo-1-(4-chloro-2-methoxyphenyl)propan-1-one in 15 ml of ethanol is heated at reflux for 6 hours. The reaction mixture is evaporated to dryness and then, successively, the residue is taken up in water, basified with 33% sodium hydroxide and extracted with ethyl acetate. The residue is purified on a column of silica gel eluted with a 1/1 (v/v) ethyl acetate/hexane mixture, to provide 0.46 g of a yellow oil. $^1$H NMR (CDCl$_3$): 0.91 (t, J=7.3, 3H, —CH$_3$), 1.61–1.78 (m, 2H, —CH$_2$—CH$_3$), 2.02 (s, 3H, heterocycle —CH$_3$), 3.83 (s, 3H, —OCH$_3$), 3.97 (t, J=7.5, 2H, —CH$_2$—N<), 6.88 (dd, J=2.5, J=8.4, 1H, H$_5$), 7.0 (d, J=2.5, 1H, H$_3$), 7.36 (d, J=8.5, 1H, H$_6$), 7.46 (dd, J=4.2, J=8.6, 1H, H$_3$,), 7.63 (d, J=7.2, 1H, H$_4$,), 7.80 (t, J=7.9, 1H, H$_7$,), 8.17 (d, J=8.4, 1H, H$_6$,), 8.33 (d, J=8.4, 1H, H$_8$,), 8.96–8.99 (m, 1H, H$_2$,).

Formation of the hydrochloride:

A saturated solution of gaseous hydrochloric acid in diethyl ether is added to an ethereal solution of 0.46 g of the compound prepared above. An orange powder is separated off by filtration and then recrystallization is carried out from isopropanol, to obtain the expected hydrochloride melting at 142° C. 1H NMR (CDCl$_3$): 0.85 (t, J=7.2, 3H, —CH$_2$—CH$_3$), 1.62 (sex, J=7.2, 2H, —CH$_2$—CH$_3$), 1.99 (s, —CH$_3$), 3.78 (s, 3H, —OCH$_3$), 3.92 (t, J=7.2, 2H, —N—CH$_2$—CH$_2$), 6.95 (dd, J=8.4, J=2.2, 1H, H$_{5ph}$), 7.08 (d, J=2.2, 1H, H$_{3ph}$), 7.30 (d, J=8.4, 1H, H$_{6ph}$h), 7.80–8.00 (m, 2H, H$_3$, and H$_4$,), 8.09 (t, J=7.8, 1H, H$_7$,), 8.36 (d, J=8.1, 1H, H$_6$,), 8.70 (d, J=8.4, 1H, H$_8$,), 9.20 (d, J=4.4, 1H, H$_2$,)

EXAMPLE 3

4-(2,4-Dichlorophenyl)-5-methyl-2-[N-(1-(methoxymethyl)-1-(naphth-2-yl)methyl)-N-propylamino]thiazole.

(I): $R_1=R_2=Cl$; $R_3=H$; $R_4=CH_3$; $R_5=$—$CH_2CH_2CH_3$; n=1; $R_6=$—$CH_2OCH_3$;

Z = 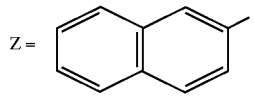

0.93 g of 2-bromo-1-(2,4-dichlorophenyl)propan-1-one, 1 g of N-(1-naphth-2-yl-2-methoxyethyl)-N-propyl-thiourea and 0.47 ml of triethylamine are dissolved in 20 ml of ethanol and the reaction mixture is heated for 3 hours at 70° C. The ethanol is removed by evaporation and then, successively, water is added, extraction is carried out with methylene chloride and the organic phases are washed, dried over sodium sulphate, filtered and concentrated under vacuum. The residue is purified on a column of silica gel, using a 9/1 (v/v) cyclohexane/ethyl acetate mixture as eluent, to provide 0.9 g of the expected product, the hydrochloride of which is prepared; M.p.=50° C. $^1$H NMR (DMSO): 0.73 (m, 3H), 1.12–1.59 (m, 2H), 2.09 (s, 3H), 3.35 (s, 3H), 3.31–3.46 (m, 2H), 3.97–4.23 (m, 2H), 5.48–5.60 (m, 1H), 7.48–7.95 (m, 10H).

EXAMPLE 4

4-(2,4-Dichlorophenyl)-5-methyl-2-[N-(6-methoxyisoquinol-5-yl)-N-propylamino]thiazole oxalate.

(I): $R_1=R_2=Cl$; $R_3=H$; $R_4=CH_3$; $R_5=$—$CH_2CH_2CH_3$; n=0;

Z = 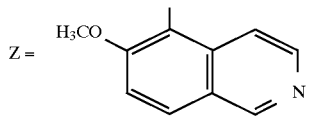

Stage 1: A methanolic solution containing 0.5 g of N-[6-methylisoquinol-5-yl]thiourea (Compound 35) and 0.6 g of 2-bromo-1-(2,4-dichlorophenyl)propan-1-one is heated at reflux. The mixture is evaporated to dryness, the residue is taken up in a saturated potassium bicarbonate solution and then extracted with dichloromethane and the organic phase is dried over sodium sulphate and evaporated to dryness, to obtain 0.3 g of pale-yellow crystals melting at 187–1880C. $^1$H NMR (CDCl$_3$): 1.99 (s, 3H, —CH$_3$), 4.02 (s, 3H, —OCH$_3$), 6.52 (dd, J=8.4, J=1.8, 1H, H$_b$), 6.87 (d, J=1.8, 1H, H$_a$), 7.03 (d, J=8.4, 1H, H$_c$) 7.39 (d, J=9.1, 1H, H$_7$,), 7.71 (d, J=5.8, 1H, H$_4$), 7.94 (d, J=9.1, 1H, H$_8$,) 8.40 (d, J=6.2, 1H, H$_3$,), 9.15 (s, 1H, H$_1$,)

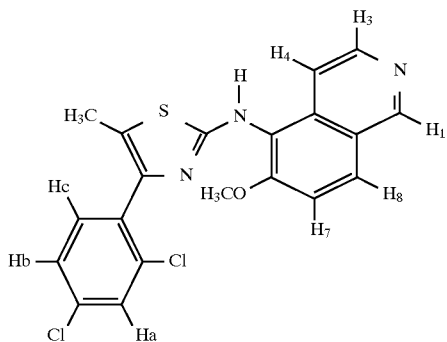

Stage 2: 0.05 g of 55% NaH is added to a solution of 0.3 g of the amine prepared above according to Stage 1 in 50 ml of anhydrous dimethylformamide and the reaction mixture is left stirring under argon for 15 minutes, before adding 0.3 ml of 1-bromopropane. The mixture is then heated at 80° C. for 2 hours, 1 equivalent of NaH and 1 equivalent of bromopropane are then added and the reaction mixture is left stirring at room temperature for 12 hours. Evaporation is carried out to dryness and the residue is taken up in a saturated sodium hydrogen-carbonate solution and extracted with dichloromethane. The organic phase is evaporated to dryness and the residue purified on a column of silica gel eluted with a 9/1 (v/v) ethyl acetate/methanol mixture, to obtain 0.3 g of a viscous oil. $^1$H NMR (CDCl$_3$): 0.86 (t, J=7.3, 3H, —CH$_2$—CH$_3$), 1.61 (sex, J=7.3, 2H, —CH$_2$—CH$_3$), 1.99 (s, 3H, —CH$_3$), 3.80 (m, 2H, —N—CH$_2$), 4.02 (s, 3H, —OCH$_3$), 7.25 (dd, J=8.4, J=2.1, 1H, H$_b$), 7.40 (d, J=8.4, 1H, H$_c$), 7.43 (d, J=2.1, 1H, H$_a$) 7.44 (d, J=9.1, 1H, H$_7$), 7.68 (d, J=5.8, 1H, H$_4$), 8.03 (d, J=9.1, 1H, H$_8$), 8.46 (d, J=5.8, 1H, H$_3$), 9.19 (S, 1H, H$_1$).

Formation of the oxalate 0.06 g of oxalic acid, dissolved in the minimum amount of isopropanol, is added to an ethereal solution of 0.3 g of the aminothiazole prepared above according to Stage 2. The precipitate obtained is recrystallized from isopropanol to provide pale-yellow crystals melting at 162–163° C. $^1$H NMR (DMSO): 0.82 (t, J=7.3, 3H, —CH$_2$—CH$_3$), 1.57 (sex, J=7.3, 2H, —CH$_2$—CH$_3$), 1.96 (s, 3H, —CH$_3$), 3.75 (m, 2H, —N—CH$_2$—), 4.00 (s, 3H, —OCH$_3$), 7.46 (m, 2H, H$_b$ and H$_c$), 7.57 (d, J=6.2, 1H, H$_4$), 7.66 (d, J=1.1, 1H, H$_a$), 7.78 (d, J=8.7, 1H, H$_7$), 8.30 (d, J=9.1, 1H, H$_e$), 8.45 (d, J=5.5, 1H, H$_3$), 9.31 (s, 1H, H$_1$).

EXAMPLE 5

4-(2-Chloro-4-methoxyphenyl)-5-methyl-2-[N-(6-methylisoquinol-5-yl)-N-propylamino]thiazole oxalate.

(I) $R_1=Cl$; $R_2=OCH_3$; $R_3=H$; $R_4=CH_3$; $R_5=$—$CH_2CH_2CH_3$; m=0;

Z = 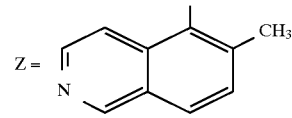

Stage 1: 1.5 g of N-[6-methylisoquinol-5-yl]thiourea (Compound 36) are dissolved in 40 ml of methanol, 2.1 g of 2-bromo-1-(2-chloro-4-methoxyphenyl)propan-1-one are then added and the reaction mixture is heated at reflux for 12 hours. Evaporation is carried out to dryness, the residue is taken up in a saturated sodium hydrogencarbonate solution and then, successively, the residue is extracted with ethyl acetate and the organic phase is dried over sodium sulphate, filtered and concentrated under vacuum. The residue is purified by chromatography on a column of silica gel, elution being carried out with a 75/25 (v/v) ethyl acetate/hexane mixture, to obtain, after concentrating the pure fractions, 1.3 g of a yellow powder of 4-(2-chloro-4-methoxyphenyl)-5-methyl-2-[N-(6-methylisoquinol-5-yl) amino]thiazole. $^1$H NMR (CDCl$_3$): 1.95 (s, 3H, —CH$_3$), 2.52 (s, 3H, —CH$_3$), 3.57 (s, 3H, —OCH$_3$), 5.96 (dd, J=8.4, J=1.8, 1H, H$_4$), 6.23 (d, J=1.8, 1H, H$_2$), 6.86 (d, J=8.4, 1H, H$_5$), 7.45 (d, J=8.4, 1H, H$_7$), 7.79 (m, 2H, H$_4$, H$_8$), 8.44 (d, J=5.8, 1H, H$_3$), 9.16 (s, 1H, H$_1$).

Stage 2: 1.3 g of the amine prepared above according to Stage 1 are added to a solution of 0.2 g of 55% NaH in 20 ml of anhydrous dimethylformamide and the reaction mixture is left stirring under argon for 15 minutes before adding 0.6 ml of 1-bromopropane. The reaction mixture is stirred at room temperature for 1 hour, 100 ml of a saturated NH₄Cl solution are added and then, successively, extraction is carried out with ethyl acetate, this phase is washed with a saturated NaCl solution and evaporated to dryness and the residue is purified on a column of silica gel eluted with a 25/75 (v/v) ethyl acetate/hexane mixture, to obtain, after concentrating the pure fractions, 0.8 g of a yellow oil. $^1$H NMR (CDCl₃): 0.88 (t, J=7.3, 3H, —CH₂—CH₃), 1.66–1.78 (m, 2H, —CH₂, —CH₃), 2.03 (s, 3H, —CH₃), 2.52 (s, 3H, —CH₃), 3.87–3.90 (m, 2H, —N—CH₂—), 4.86 (s, 3H, —OCH₃), 6.86 (dd, J=8.4, J=2.5, 1H, H₅), 7.00 (d, J=2.5, 1H, H₃), 7.39 (d, J=8.8, 1H, H₆), 7.57 (d, J=8.4, 1H, H₇), 7.70 (d, J=5.8, 1H, H₄), 7.94 (d, J=8.4, 1H, H₈), 8.54 (d, J=5.8, 1H, H₃), 9.27 (s, 1H, H₁).

Formation of the oxalate 0.16 g of oxalic acid, dissolved in the minimum amount of isopropanol, is added to a solution of 0.8 g of the aminothiazole prepared above according to Stage 2 in the minimum amount of ether and petroleum ether, to obtain yellow crystals of the expected product. $^1$H NMR (DMSO): 0.82 (t, J=7.3, 3H, —CH₂—CH₃), 1.64 (m, 2H, —CH₂—CH₃), 1.96 (s, 3H, —CH₃), 2.44 (s, 3H, —CH₃), 3.76–3.79 (m, 2H, —N—CH₂), 3.79 (s, 3H, —OCH₃), 6.94 (dd, J=2.5, J=8.4, 1H, H₅), 7.08 (d, J=2.5, 1H, H₃), 7.33 (d, J=8.8, 1H, H₆), 7.62 (d, J=8.4, 1H, H₇), 7.72 (d, J=5.8, 1H, H₄), 8.15 (d, J=9.1, 1H, H₈), 8.53 (d, J=5.5, 1H, H₃), 9.38 (s, 1H, H₁).

EXAMPLE 6

4-(2,4-Dichlorophenyl)-5-methyl-2-[N-(1-(cyclopropyl)-1-(quinol-4-yl)methyl)-N-propylamino]thiazole oxalate.

(I): R₁=R₂=Cl; R₃=H; R₄=CH₃; R₅=—CH₂CH₂CH₃; n=1;

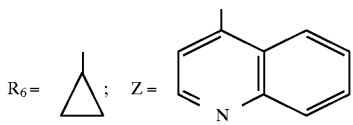

Stage 1: 3.0 g of 4-quinolinecarboxaldehyde and 5.0 g of ²-amino-4-(2,4-dichlorophenyl)-5-methylthiazole are dissolved in 50 ml of benzene in a round-bottomed flask equipped with a Dean and Stark apparatus. The reaction mixture is maintained at reflux for 24 hours. Evaporation is carried out to dryness and the residue is taken up in a saturated sodium hydrogencarbonate solution and extracted with dichloromethane. Evaporation is carried out to dryness and the residue is purified by chromatography on a column of silica gel eluted with ethyl acetate +2% triethylamine. Concentrating the pure fractions provides 8.2 g of vivid yellow crystals melting at 140°–141° C. of 4-(2,4-dichlorophenyl)-5-methyl-2-[N-(quinol-4-ylmethyl)imino]thiazole. $^1$H NMR (CDCl₃): 2.27 (s, 3H, —CH₃), 7.23 (dd, J=7.6, J=1.8, 1H, H$_b$), 7.29 (d, J=7.6, 1H, H$_c$), 7.43 (d, J=1.8, 1H, H$_a$), 7.53 (td, J=8.4, J=1.4, 1H, H₅), 7.65 (td, J=8.4, J=1.4, 1H, H₄), 7.84 (d, J=4.4, 1H, H₂), 8.07 (d, J=8.4, 1H, H₃), 8.75 (d, J=8.4, 1H, H₆), 8.92 (d, J=4.4, 1H, H₁), 9.51 (a, 1H, —N═CH—).

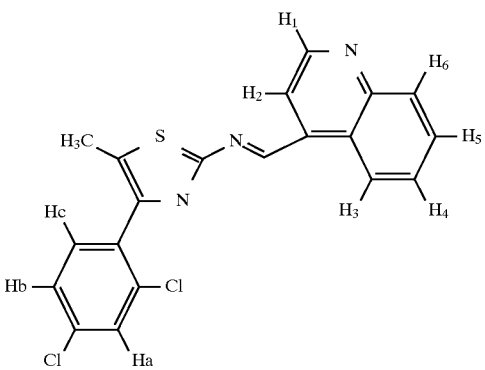

Stage 2: 8.5 g of the imine prepared above according to Stage 1, diluted in anhydrous tetrahydrofuran, are slowly added, in a three-necked flask maintained under argon, to a solution containing an organo-magnesium compound obtained from 1.0 g of magnesium and 4.8 g of cyclopropyl bromide. The excess magnesium compound is destroyed by addition of a saturated ammonium chloride solution and extraction is carried out with diethyl ether. Evaporation is carried out to dryness and the residue is purified by chromatography on a column of silica gel eluted with ethyl acetate, to obtain, after concentrating the pure fractions, 5.1 g of a very viscous yellow oil of 4-(2,4-dichlorophenyl)-5-methyl-2-[N-(1-(cyclopropyl)-1-(quinol-4-yl)methyl)amino]thiazole. $^1$H NMR (CDCl₃): 0.40–0.65 (m, 4H, —CH₂—CH₂), 1.15–1.35 (m, 1H, —CH—CH—CH₂), 2.03 (s, 3H, —CH₃), 4.93 (dd, J=8.1, J=3.9, 1H, —NH—CH—), 6.31 (d, J=4.0, 1H, —NH—CH—), 7.23 (dd, J=7.6, J=1.8, 1H, H$_b$), 7.29 (d, J=8.4, 1H, H$_c$), 7.43 (d, J=1.8, 1H, H$_a$) 7.53 (J=8.4, J=1.4) 1H, H₅), 7.65 (td, J=8.4, J=1.4, 1H, H₄), 7.84 (d, J=4.4, 1H, H₂), 8.07 (d, J=8.4, 1H, H₃), 8.75 (d, J=8.4, 1H, H₆), 8.92 (d, J=4.4, 1H, H₁).

Stage 3: 0.6 g of 55% NaH is added to a solution of 5.46 g of the amine prepared according to Stage 2 in 50 ml of anhydrous dimethylformamide and the reaction mixture is left stirring under argon for 15 minutes before adding 1.8 g of 1-bromopropane. The reaction mixture is heated at 80° C. for 2 hours, one equivalent of NaH and 1 equivalent of bromopropane are added and the reaction mixture is left stirring at room temperature for 12 hours. Evaporation is carried out to dryness and the residue is taken up in a saturated sodium hydrogencarbonate solution and extracted with dichloromethane. Evaporation is carried out to dryness and the residue is purified by chromatography on a column of silica gel eluted with ethyl acetate, to obtain 0.79 g of a colourless oil of the expected product. $^1$H NMR (CDCl₃): 0.35–0.75 (m, 7H, where (t, J=7.6, 3H, —CH₂—CH₃) is recognized at 0.71, —CH₂—CH₂), 1.15–1.35 (m, 1H, CH—CH₂—CH₂), 1.68 (sex, J=7.6, 2H, —CH₂—CH₃), 2.10 (s, 3H, —CH₃), 3.14 (m, J=7.6, 2H, —N—CH₂), 5.58 (d, J=9.9, 1H, —N—CH—), 7.20 (dd, J=8.4, J=1.8, 1H, H$_b$), 7.29 (d, J=8.4, 1H, H$_c$), 7.35 (td, J=8.4, J=1.4, 1H, H₅), 7.40 (d, J=1.8, 1H, H$_a$), 7.55 (td, J=8.4, J=1.4, 1H, H), 7.65 (d, J=4.4, 1H, H), 8.01 (d, J=8.4, 1H, H), 8.15 (d, J=8.4, 1H, H₆), 8.84 (d, J=4.4, 1H, H₁)

Formation of the oxalate.

0.1 g of oxalic acid, diluted in the minimum amount of isopropanol, is added to a solution of diethyl ether containing 0.8 g of the aminothiazole prepared above according to Stage 3 and the precipitate obtained is then recrystallized from isopropanol, to obtain yellow crystals melting at 164°–165° C. $^1$H NMR (DMSO): 0.35–0.75 (m, 7H, where (t, J=7.6, 3H, —CH$_2$—CH$_3$) is recognized at 0.71, —CH$_2$—CH$_2$), 1.15–1.35 (m, 1H, CH—CH—CH$_2$) 1.68 (sex, i=7.6, 2H, —CH$_2$—CH$_3$), 2.10 (s, 3H, —CH$_3$), 3.14 (m, J=7.6, 2H, —N—CH$_2$), 5.46 (d, J=10.2, 1H, —N—CH—), 7.30–7.50 (m, 3H, H$_a$, H$_b$, and H$_c$), 7.65–7.80 (m, 2H, H$_5$ and H$_4$), 7.92 (d, J=3.6, 1H, H$_2$), 8.02 (d, J=7.7, 1H, H$_3$), 8.21 (d, J=8.4, 1H, H$_6$), 8.95 (d, J=3.6, 1H, H$_1$).

EXAMPLE 7

4-(2-Chloro-4-methoxyphenyl)-5-methyl-2-[N-(indol-5-yl)-N-propylamino]thiazole.

(I): R$_1$=Cl; R$_2$=OCH$_3$; R$_3$=H; R$_4$=CH$_3$; R$_5$=—CH$_2$CH$_2$CH$_3$; n=0;

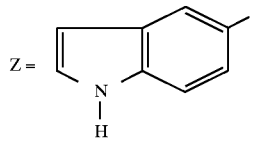

Stage 1: 10.9 g of 4-(2-chloro-4-methoxyphenyl)-5-methyl-2-[N-(1-(tetrahydropyran-2-yl)indol-5-yl)amino]-thiazole are dissolved in 110 ml of dimethylformamide. 1.06 g of 60% sodium hydride in oil and then 3.2 ml of propyl bromide are added at 0° C. After stirring for 16 hours at room temperature, the reaction mixture is poured onto 500 ml of water and extracted 3 times with 250 ml ethyl acetate. The organic phase is washed with 3 times 200 ml of water, dried over sodium sulphate and evaporated to dryness. The residue is purified by flash chromatography on silica gel eluted with a 3/1 (v/v) cyclohexane/ethyl acetate mixture. 10.17 g of the expected product (85%) are obtained. $^1$H NMR (CDCl$_3$): 0.90 (m, 3H), 1.57–1.75 (m, 6H), 2.02 (s, 3H), 1.95–2.25 (m, 2H), 3.70–4.17 (m, 7H), 5.50 (dd, J=2.6, 10.0, 1H), 6.54–7.61 (m, 8H).

Stage 2:

8 ml of a 35% hydrochloric acid solution are added to 6.6 g of 4-(2-chloro-4-methoxyphenyl)-5-methyl-2-[N-(1-(tetrahydropyran-2-yl)indol-5-yl)-N-propylamino]-thiazole in solution in 50 ml of methanol. The reaction mixture is stirred for 24 hours and is then diluted with water and neutralized with a 30% sodium hydroxide solution. The mixture is extracted with dichloromethane. The organic phase is washed several times with water and dried over sodium sulphate. After evaporating the solvent, the residue is purified by chromatography on a column of silica gel eluted with a stepwise gradient from 10 to 50% of ethyl acetate in cyclohexane. 3.5 g of protected product are isolated and 0.85 g of the expected product are isolated in the form of a white solid; M.p.=154° C. $^1$H NMR (DMSO): 0.83 (m, 3H), 1.42–1.65 (m, 2H), 1.96 (s, 3H), 3.74 (s, 3H), 3.59–3.89 (m, 2H), 6.35 (d, J=3.2, 1H), 6.94 (dd, J=2.6, 8.6, 1H), 7.02–7.08 (m, 2H), 7.31 (d, J=8.5, 1H), 7.38–7.42 (m, 1H), 7.43 (d, J=8.6, 1H), 7.55 (d, J=2.0, 1H).

EXAMPLE 8

4-(2-Chloro-4-methoxyphenyl)-5-methyl-2-[N-(1-methylindol-5-yl)-N-propylamino]thiazole.

(I): R$_1$=Cl; R$_2$=OCH$_3$; R$_3$=H; R$_4$=CH$_3$; R$_5$=—CH$_2$CH$_2$CH$_3$; n=0;

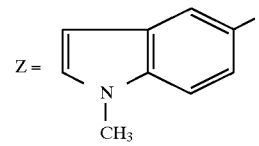

0.045 g of 55% sodium hydride in oil and then 0.12 ml of methyl iodide are added, at 4° C., to 0.39 g of 4-(2-chloro-4-methoxyphenyl)-5-methyl-2-[N-(indol-5-yl)-N-propylamino]thiazole obtained above (EXAMPLE 7) in solution in 5 ml of dimethylformamide. After stirring for 5 hours at room temperature, the reaction mixture is poured into ice-cold water. The mixture is extracted with ethyl acetate and the organic phase is washed a number of times with water, dried over sodium sulphate and evaporated to dryness. The residue is purified by chromatography on a column of silica gel eluted with a 9/1 (v/v) cyclohexane/ethyl acetate mixture. The expected product is isolated in the form of a white solid; M.p.=146° C. $^1$H NMR (CDCl$_3$): 0.92 (m, 3H), 1.58–1.73 (m, 2H), 2.01 (s, 3H), 3.81–4.0 (m, 8H), 6.51 (d, J=2.8, 1H), 6.85 (dd, J=2.2, 8.4, 1H), 6.99 (d, J=2.0, 1H), 7.09–7.20 (m, 2H), 7.35–7.40 (m, 2H), 7.62 (s, 1H).

EXAMPLE 9

4-(2-Chloro-4-methoxyphenyl)-5-methyl-2-[N-(1-methoxycarbonylmethylindol-5-yl)-N-propylamino] thiazole.

(I): R$_1$=Cl; R$_2$=OCH$_3$; R$_3$=H; R$_4$=CH$_3$; R$_5$=—CH$_2$CH$_2$CH$_3$; n=0;

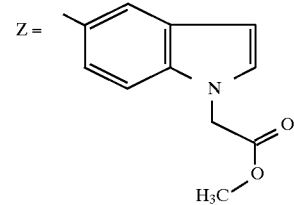

0.093 g of 55% sodium hydride in oil and then 0.95 ml of methyl bromoacetate are added, at 0° C., to 0.8 g of 4-(2-chloro-4-methoxyphenyl)-5-methyl-2-[N-(indol-5-yl)-N-propylamino]thiazole obtained above (EXAMPLE 7) in solution in 20 ml of dimethylformamide. After stirring for twelve hours at room temperature, the reaction mixture is poured into ice-water. The mixture is extracted with ethyl acetate and the organic phase is washed a number of times with water, dried over sodium sulphate and evaporated to dryness. The residue is purified by chromatography on a column of silica gel eluted with a 9/1 (v/v) cyclohexane/ethyl acetate mixture. The expected product is isolated in the form of a white solid (Y=95%); M.p.=80° C. $^1$H NMR (DMSO): 0.84 (t, 3H), 1.51–1.62 (m, 2H), 1.94 (s, 3H), 3.68 (s, 3H), 3.79 (s, 3H), 3.75–3.82 (m, 2H), 5.17 (s, 2H), 6.50 (d, 1H), 6.91–7.58 (m, 7H).

EXAMPLE 10

4-(2-Chloro-4-methoxyphenyl)-5-methyl-2-[N-(1-(1-(methoxycarbonyl) ethyl) indol-5-yl)-N-propylamino] thiazole hydrochloride.

(I): R$_1$=Cl; R$_2$=OCH$_3$; R$_3$=H; R$_4$=CH$_3$; R$_5$=—CH$_2$CH$_2$CH$_3$; n=0;

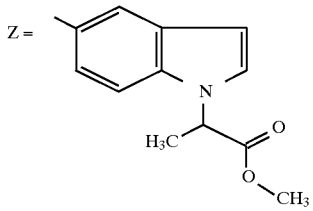

Stage 1: 0.14 g of 55% sodium hydride in oil and then 1.6 ml of methyl 2-bromopropionate are added, at 0° C. under argon, to 1.2 g of 4-(2-chloro-4-methoxyphenyl)-5-methyl-2-[N-(indol-5-yl)-N-propylamino]thiazole obtained above (EXAMPLE 7) in solution in 20 ml of methanol. After stirring for 24 hours, the reaction mixture is poured onto ice-cold water and extracted with ethyl acetate. After drying and evaporating to dryness under vacuum, the residue is taken up in 20 ml of methanol. After the addition of 1.1 ml of a 2N sodium hydroxide solution, the mixture is stirred for 24 hours, the ethanol is then evaporated and the residue is taken in $H_2O$, brought to pH=6 by addition of a 2N HCl solution and extracted with ethyl acetate. The organic phase is washed a number of times, dried over sodium sulphate and evaporated. The solid residue is purified by chromatography on a column of silica gel eluted with a 98/2 (v/v) $CH_2Cl_2$/$CH_3OH$ mixture. 0.80 g of the corresponding acid is obtained.

Stage 2: 0.294 g of $Cs_2CO_3$ and then 0.31 ml of methyl iodide are added to 0.8 g of the product obtained above in solution in 15 ml of dimethylformamide. After stirring for 3 hours, the reaction mixture is diluted with ethyl acetate, washed a number of times with water saturated with sodium chloride, dried over sodium sulphate and then evaporated to dryness under vacuum. The residue is purified by chromatography on a column of silica gel eluted with a 5/1 (v/v) cyclohexane/ethyl acetate mixture. The expected product is isolated in the form of a colourless oil (0.66 g) . The hydrochloride monohydrate is obtained, by addition of a 0.1N solution of HCl in isopropanol, in the form of a white solid; M.p.=80° C. $^1$H NMR ($CDCl_3$): 0.92 (t, 3H), 1.62–1.74 (m, 2H), 1.83 (d, 3H), 2.02 (s, 3H), 3.74 (s, 3H), 3.81 (s, 3H), 3.88–3.98 (m, 2H), 5.13–5.20 (m, 1H), 6.59 (d, 1H), 6.82–7.62 (m, 7H).

EXAMPLE 11

4-(2-Chloro-4-methoxyphenyl)-5-methyl-2-[N-(1-carboxymethylindol-5-yl)-N-propylamino]thiazole.

(I): $R_1$=Cl; $R_2$=$OCH_3$; $R_3$=H; $R_4$=$CH_3$; $R_5$=—$CH_2CH_2CH_3$; n=0;

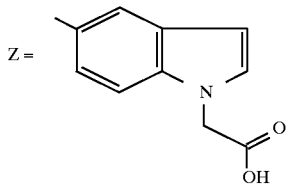

1.2 ml of a 1M aqueous sodium hydroxide solution are added to 0.52 g of the product obtained above (EXAMPLE 9) in solution in 10 ml of ethanol. After stirring for 18 hours at room temperature, the ethanol is evaporated and the residue is taken up in water, brought to pH=6 by addition of a 2N HCl solution and then extracted with dichloromethane. The organic phase is washed with a solution saturated with NaCl, dried over sodium sulphate and evaporated. The solid residue is purified by chromatography on a column of silica gel eluted with a 92/8 (v/v) $CH_2Cl_2$/$CH_3OH$ mixture. The expected product is isolated in the form of a white solid (hemihydrate); M.p.=120° C. $^1$H NMR (DMSO): 0.88 (t, 3H), 1.51–1.62 (m, 2H), 1.93 (s, 3H), 3.78 (s, 3H), 3.74–3.82 (m, 2H), 4.48 (s, 2H), 6.38 (d, 1H), 6.91–7.51 (m, 7H).

EXAMPLE 12

4-($^2$-Chloro-4-methoxyphenyl)-5-methyl-2-[N-(1-morpholinocarbonylmethylindol-5-yl)-N-propylamino]-thiazole hydrochloride.

(I): $R_1$=Cl; $R_2$=$OCH_3$; $R_3$=H; $R_4$=$CH_3$; $R_5$=—$CH_2CH_2CH_3$; n=0;

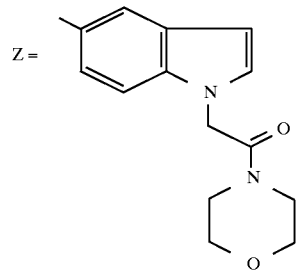

0.36 ml of triethylamine and then 0.34 ml of isobutyl chloroformate are added, at –10° C. under argon, to 1.1 g of the product obtained above (EXAMPLE 11) in solution in 20 ml of dimethylformamide. After stirring for 10 minutes at –10° C., 0.74 ml of freshly distilled morpholine is added. After 2 hours at –10° C., the reaction mixture is allowed to return to room temperature and the organic phase is then diluted with ethyl acetate. The organic phase is washed a number of times with water, dried over sodium sulphate and evaporated. The residue is purified by chromatography on a column of silica gel eluted with a 98/2 (v/v) $CH_2Cl_2$/$CH_3OH$ mixture. The hydrochloride obtained in the hydrated form (dihydrate) is prepared by using a 0.1N solution of HCl in isopropanol; M.p.=134° C. $^1$H NMR ($CDCl_3$): 0.93 (t, 3H), 1.59–1.77 (m, 2H), 1.99 (s, 3H), 2.85–2.93 (m, 4H), 3.43–3.47 (m, 4H), 3.80 (s, 3H), 3.88–4.15 (m, 2H), 4.93 (s, 2H), 6.59 (d, 1H), 6.81–7.60 (m, 7H).

EXAMPLE 13

4-(2-Chloro-4-methoxyphenyl)-5-methyl-2-[N-(1-(methylcarbonylmethyl)indol-5-yl)-N-propylamino]thiazole hydrochloride.

(I): $R_1$=Cl; $R_2$=$OCH_3$; $R_3$=H; $R_4$=$CH_3$; $R_5$=—$CH_2CH_2CH_3$; n=0;

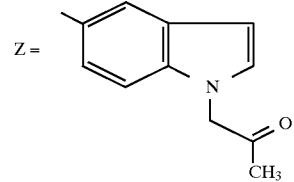

Stage 1: 0.35 g of 55% sodium hydride in oil and then 1 ml of bromoacetonitrile are added, at 0° C. under argon, to 1.1 g of 4-(2-chloro-4-methoxyphenyl)-5-methyl-2-[N-(indol-5-yl)-N-propylamino]thiazole obtained above (EXAMPLE 7) in solution in 10 ml of dimethylformamide.

After stirring for 18 hours at room temperature, the reaction mixture is poured into ice-cold water. The mixture is extracted with ethyl acetate and the organic phase is washed a number of times with water, dried over sodium sulphate and evaporated to dryness. The residue is purified by chromatography on a column of silica gel eluted with a 9/1 (v/v) cyclohexane/ethyl acetate mixture.

Stage 2: 1.3 ml of a 1.4M solution of methylmagnesium bromide are added, at 0° C., to 0.66 g of the product obtained in the preceding stage in solution in 10 ml of anhydrous diethyl ether. After 5 hours at room temperature, the reaction mixture is hydrolysed by addition of a saturated ammonium chloride solution. The mixture is extracted with ethyl acetate and the organic phase is washed a number of times with water, dried and then evaporated to dryness. The residue is purified by chromatography on a column of silica gel eluted with a 98/2 (v/v) $CH_2CL_2/CH_3OH$ mixture. The expected product is isolated in the form of an oil. The hydrochloride is obtained, by addition of a 0.1M solution of HCl in isopropanol, in the form of a monohydrate white solid; M.p.=189° C. $^1$H NMR ($CDCl_3$): 0.90 (t, 3H), 1.41 (s, 3H), 1.57–1.68 (m, 2H), 2.01 (s, 3H), 2.10 (s, 2H), 3.81 (s, 3H), 3.85–3.92 (m, 2H), 6.60–7.63 (m, 8H).

EXAMPLES 14 and 15

4-(2-Chloro-4-methoxyphenyl)-5-methyl-2-[N-(1-propylindazol-6-yl)-N-propylamino]thiazole (EXAMPLE 14).

4-(2-Chloro-4-methoxyphenyl)-5-methyl-2-[N-(2-propylindazol-6-yl)-N-propylamino]thiazole (EXAMPLE 15).

(I): $R_1$=Cl; $R_2$=$OCH_3$; $R_3$=H; $R_4$=$CH_3$; R5=—$CH_2CH_2CH_3$; n=0;

(EXAMPLE 14)

Z = 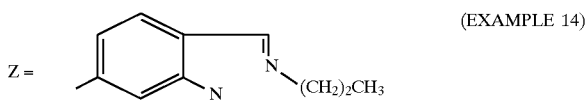

or Z = 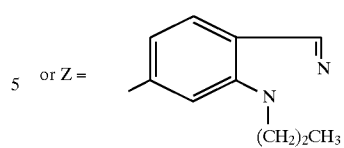 (EXAMPLE 15)

0.24 g of 55% sodium hydride in suspension in oil and then, after stirring for 10 minutes, 0.55 ml of propyl bromide are added, at 0° C., to 0.94 g of 4-(2-chloro-4-methoxyphenyl)-5-methyl-2-[N-indazol-6-ylamino]-thiazole in solution in 20 ml of dimethylformamide. After stirring for 1 hour 30 at room temperature, the reaction mixture is poured onto 100 ml of ice-cold water and extracted with ethyl acetate. The organic phase is washed with 4 times 100 ml of water, dried over sodium sulphate and evaporated under vacuum. The residue is purified by chromatography on a column of silica gel eluted with a 4/1 (v/v) cyclohexane/ethyl acetate mixture. 0.34 g of 4-(2-chloro-4-methoxyphenyl)-5-methyl-2-[N-(1-propylindazol-6-yl)-N-propylamino]thiazole is obtained in the form of an oil and 0.28 g of 4-(2-chloro-4-methoxy-phenyl)-5-methyl-2-[N-(2-propylindazol-6-yl)-N-propyl-amino]thiazole is obtained in the form of an oil.

$^1$H NMR ($CDCl_3$) EXAMPLE 14: 0.88–1.08 (m, 6H), 1.62–1.81 (m, 2H), 1.95–2.14 (m, 5H), 3.81 (s, 3H), 3.90–3.98 (m, 2H), 4.36 (t, J=7.0, 2H), 6.84 (dd, J=2.6, 8.4, 1H), 6.97 (d, J=2.4, 1H), 7.10 (dd, J=1.7, 8.9, 1H), 7.33 (d, J=8.6, 1H), 7.69–7.88 (m, 2H), 7.90 (s, 1H).

$^1$H NMR ($CDCl_3$) EXAMPLE 15: 0.89–0.98 (m, 6H), 1.63–1.82 (m, 2H), 1.83–2.05 (m, J=7.0, 2H), 2.08 (s, 3H), 3.82 (s, 3H), 3.93–4.00 (m, 2H), 4.32 (t, J=7.0, 2H), 6.85 (dd, J=2.6, 8.4, 1H), 6.98 (d, J=2.6, 1H), 7.14 (dd, J=1.8, 8.6, 1H), 7.34 (d, J=8.6, 1H), 7.48 (m, 1H), 7.75 (d, J=8.6, 1H), 7.98 (s, 1 H).

TABLE I

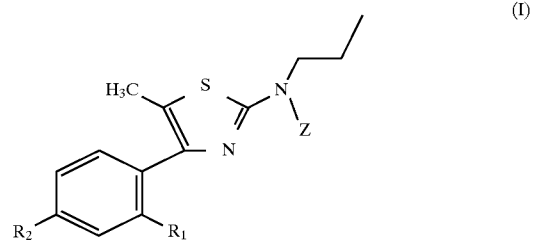

(I)

| Example Number | —$R_1$ | —$R_2$ | Z | Route | M.p. (°C.), salt |
|---|---|---|---|---|---|
| 16 | $OCH_3$ | Cl | 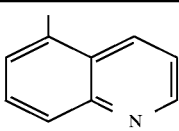 | A | 142, HCl |
| 17 | $OCH_3$ | Br | 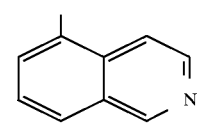 | A | 148, $H_2C_2O_4$ |

TABLE I-continued (I) Structure: H₃C−C(S−)=C(Ar)−N=C(−N(propyl)(Z)) where Ar is phenyl substituted with R₁ (ortho) and R₂ (para).

| Example Number | −R₁ | −R₂ | Z | Route | M.p. (°C.), salt |
|---|---|---|---|---|---|
| 18 | Br | OCH₃ | 5-methylisoquinolinyl | A | 159, H₂C₂O₄ |
| 19 | OCH₃ | Cl | 6-methylquinolinyl | A | 159, H₂C₂O₄ |
| 20 | Cl | OCH₃ | 5-methylquinolinyl | A | 172, H₂C₂O₄ |
| 21 | Cl | CH₃ | 5-methylisoquinolinyl | A | 167, H₂C₂O₄ |
| 22 | CH₃ | Cl | 5-methylisoquinolinyl | A | 182, H₂C₂O₄ |
| 23 | Cl | Cl | 5-methylquinolinyl | A | 119, H₂C₂O₄ |
| 24 | OCH₃ | Cl | 1-methylnaphthyl | A | —, base |
| 25 | Cl | Cl | 1-methylnaphthyl | A | oil, base |
| 26 | Cl | OCH₃ | 5-methylquinolinyl | A | 211, HCl |
| 27 | Cl | OCH₃ | 6-methoxy-5-methylisoquinolinyl | B | 101, H₂C₂O₄ |

TABLE I-continued (I)

[Structure: H₃C-C(=C(-aryl)-N=C(-S)-N(-propyl)(-Z)) where aryl is a phenyl ring bearing R₂ (para) and R₁ (ortho)]

| Example Number | −R₁ | −R₂ | Z | Route | M.p. (°C.), salt |
|---|---|---|---|---|---|
| 28 | OCH₃ | Cl | 5-methyl-6-methoxyisoquinolinyl | B | 160, base |
| 29 | Cl | OCH₃ | 6-chloro-5-methylisoquinolinyl | B | 120, H₂C₂O₄ |
| 30 | Cl | OCH₃ | 1-methyl-2-methoxynaphthyl | B | 72, H₂C₂O₄ |
| 31 | Cl | OCH₃ | 5-methyl-6-methoxyisoquinolinyl (isomer) | B | 67, H₂C₂O₄ |
| 32 | Cl | OCH₃ | methylquinazolinyl | B | 158, H₂C₂O₄ |
| 33 | Cl | OCH₃ | methylquinoxalinyl | B | 88, HCl |
| 34 | Cl | OCH₃ | 1-methoxy-2-methylnaphthyl | B | oil |
| 35 | Cl | OCH₃ | 1,4-dimethoxy... naphthyl (methyl, OCH₃) | B | 103, HCl |
| 36 | Cl | CF₃ | 5-methyl-6-methylisoquinolinyl | B | 115, H₂C₂O₄ |
| 37 | Cl | CF₃ | 5-methyl-6-methoxyisoquinolinyl | B | H₂C₂O₄ |

TABLE I-continued (I)

| Example Number | −R₁ | −R₂ | Z | Route | M.p. (°C.), salt |
|---|---|---|---|---|---|
| 38 | Cl | OCH₃ | 6-chloro-5-methyl-2-methylquinoline | B | 168, H₂C₂O₄ |
| 39 | Cl | OCH₃ | 6-methoxy-5-methylquinoxaline | B | 68, HCl |
| 40 | Cl | OCH₃ | 2-ethoxy-1-methylnaphthalene | B | 86, HCl |
| 41 | Cl | OCH₃ | 2-propoxy-1-methylnaphthalene | B | 105, HCl |
| 42 | Cl | OCH₃ | 3-methoxy-4-methyl-1-ethylnaphthalene | B | 198, HCl |
| 43 | Cl | OCH₃ | 3-methoxy-4-methyl-1-isopropylnaphthalene | B | |
| 44 | Cl | OCH₃ | 1,2,3-trimethylnaphthalene | B | 117, HCl |
| 45 | Cl | OCH₃ | 6-methoxy-5-methyl-2-bromonaphthalene | B | 90, HCl |
| 46 | Cl | OCH₃ | 1,2,6-trimethylnaphthalene | B | 98, HCl |

TABLE I-continued (I) [Structure: H3C-C(S-)=C(aryl)-N=C(N(propyl)(Z))- where aryl is phenyl with R2 and R1 substituents]

| Example Number | −R₁ | −R₂ | Z | Route | M.p. (°C.), salt |
|---|---|---|---|---|---|
| 47 | Cl | OCH₃ | H₃CO-CH₂CH₂-O-(1-methylnaphthalen-2-yl) | B | 70, HCl |
| 48 | Cl | OCH₃ | 5-methylindol-1-yl-CH₂CH₂-C(=O)-O-ethyl | B | 64, HCl |
| 49 | Cl | OCH₃ | 5-methylindol-1-yl-(CH₂)₃-C(=O)-O-methyl | B | 80, HCl |
| 50 | Cl | OCH₃ | 5-methylindol-1-yl-CH₂-C(=O)-N(ethyl)₂ | B | 70, base |

TABLE II

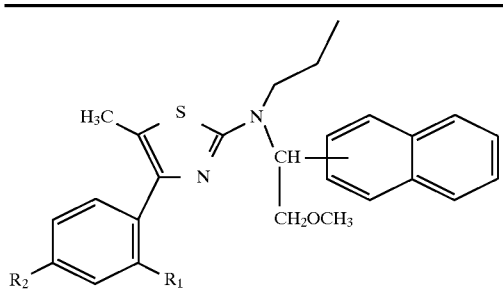

| Example Number | —R₁ | —R₂ | Naphthyl position | Route | M.p. (°C.), salt |
|---|---|---|---|---|---|
| 51 | Cl | Cl | 1 | A | 50, HCl |
| 52 | Cl | OCH₃ | 1 | A | 50, HCl |
| 53 | Cl | OCH₃ | 2 | A | 50, HCl |

TABLE III

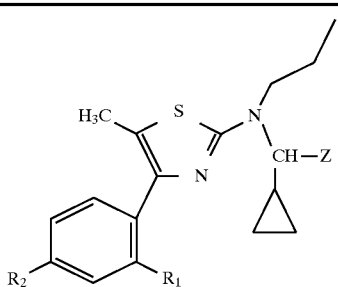

| Example Number | —R₁ | —R₂ | Z | Route | M.p. (°C.) |
|---|---|---|---|---|---|
| 54 | Cl | Cl |  | C | 164, oxalate |
| 55 | Cl | OCH₃ | 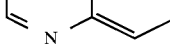 | C | 192 |

TABLE IV

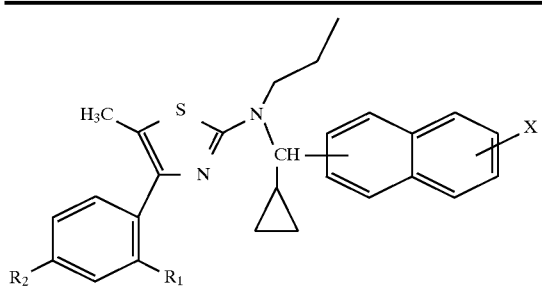

| Example number | —R₁ | —R₂ | Naphthyl position | X | Route | M.p. (°C.), salt |
|---|---|---|---|---|---|---|
| 56 | Cl | Cl | 2 | H | C | 179, HCl |
| 57 | Cl | Cl | 1 | H | C | 115, base |
| 58 | Cl | OCH₃ | 1 | H | C | 178, base |
| 59 | Cl | OCH₃ | 1 | 2-OCH₃ | C | 50, base |

TABLE IV-continued

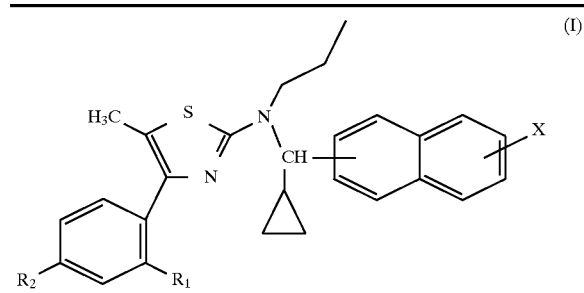

| Example number | —R₁ | —R₂ | Naphthyl position | X | Route | M.p. (°C.), salt |
|---|---|---|---|---|---|---|
| 60 | Cl | OCH₃ | 1 | 4-OCH₃ | C | 157, base |
| 61 | Cl | OCH₃ | 2 | H | C | 50, HCl |
| 62 | Cl | OCH₃ | 2 | 3-OCH₃ | C | 146, base |

We claim:
1. A compound of formula:

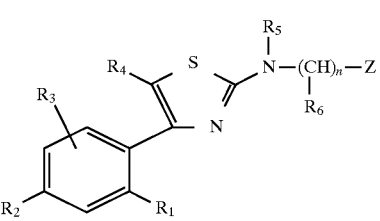

in which $R_1$, and $R_2$, which are identical or different, are independently selected from a halogen atom; a $(C_1-C_5)$ hydroxyalkyl radical; a $(C_1-C_5)$alkyl; a $(C_7-C_{10})$ aralkyl; a $(C_1-C_5)$alkoxy; a trifluoromethyl; a nitro; a nitrile; an —SR group in which R is selected from hydrogen, a $(C_1-C_5)$alkyl radical and a $(C_7-C_{10})$aralkyl radical; an —S—CO—R group in which R is selected from a $(C_1-C_5)$alkyl radical and an aralkyl radical in which the aryl part is $(C_6-C_8)$ and the alkyl part is $(C_1-C_4)$; a —COOR' group in which R' is selected from hydrogen and a $(C_1-C_5)$alkyl; a —CONR'R" group with R' and R" as defined above for R'; an —NR'R" group with R' and R" as defined above for R'; a —CONRaRb or —NRaRb group in which Ra and Rb constitute, with the nitrogen atom to which they are bonded, a 5- to 7-membered heterocycle; and an —NHCO—NR'R" group with R' and R" as defined above for R';

$R_3$ represents hydrogen or is as defined above for $R_1$ and $R_2$;

$R_4$ is selected from a hydrogen atom; a $(C_1-C_5)$alkyl; a halogen, a hydroxymethyl group; and a formyl group;

$R_5$ is selected from a $(C_1-C_5)$alkyl; a $(C_3-C_7)$cycloalkyl group; a cycloalkylalkyl group in which the cycloalkyl part is $(C_3-C_7)$ and the alkyl part is $(C_1-C_5)$; and alkenyl containing 5 to 6 carbon atoms;

n represents zero or one;

$R_6$ is selected from a $(C_1-C_5)$alkyl; an alkoxyalkyl in which the alkyl parts are $(C_1-C_5)$; a $(C_3-C_7)$cycloalkyl; a cycloalkylalkyl group in which the cycloalkyl part is $(C_3-C_7)$ and the alkyl part is $(C_1-C_5)$; a cycloalkyloxyalkyl radical in which the cycloalkyl is $(C_3-C_7)$ and the alkyl part is $(C_1-C_4)$; a hydroxyalkyloxyalkyl radical in which the alkyls are $(C_2-C_{10})$; and an alkoxyalkyloxyalkyl radical in which the alkyls are $(C_3-Cl_2)$;

Z represents an optionally substituted bi- or tricyclic aromatic or heteroaromatic group;
a stereoisomer and/or an addition salt, thereof.

2. A compound of formula (I) according to claim 1, in which Z represents a naphthyl group or a heteroaromatic group selected from quinolyl, isoquinolyl, quinazolyl, quinoxalyl, indolyl and indazolyl, said groups optionally being substituted, $R_1$, $R_2$, $R_3$, $R_4$, $R_5$, n and $R_6$ being as defined for (I), a stereoisomer and/or an addition salt, thereof.

3. A compound of formula (I) according to claim 1, in which $R_3$ represents hydrogen, $R_4$ represents a methyl, $R_5$ represents propyl, n is 0 and $R_1$, $R_2$ and Z are as defined for (I), a stereoisomer and/or an addition salt, thereof.

4. A compound of formula (I) according to claim 1, in which $R_3$ represents hydrogen, $R_4$ represents a methyl, $R_5$ represents propyl, n is 1, $R_6$ represents cyclopropyl and $R_1$, $R_2$ and Z are as defined for (I), a stereoisomer and/or an addition salt, thereof.

5. A compound of formula (I) according to claim 1, in which $R_3$ represents hydrogen, $R_4$ represents methyl, $R_5$ represents propyl, n is 1, $R_6$ represents a —$CH_2OCH_3$ group and $R_1$, $R_2$ and Z are as defined for (I), a stereoisomer and/or an addition salt, thereof.

6. A compound of formula (I) according to claim 1, in which $R_3$ represents hydrogen, $R_4$ represents methyl, $R_5$ represents propyl and $R_1$ or $R_2$ is a halogen or ($C_1$–$C_5$) alkyl or alkoxy; n, $R_6$ and Z being as defined for (I), a stereoisomer and/or an addition salt, thereof.

7. A compound according to claim 1, which is selected from
4-(2,4-dichlorophenyl)-5-methyl-2-[N-(1-(methoxymethyl)-1-(naphth-2-yl)methyl)-N-propylamino]thiazole,
4-(2,4-dichlorophenyl)-5-methyl-2-[N-(6-methoxyisoquinol-5-yl)-N-propylamino]thiazole oxalate,
4-(2-chloro-4-methoxyphenyl)-5-methyl-2-[N-(6-methylisoquinol-5-yl)-N-propylamino]thiazole oxalate,
4-(2-chloro-4-methoxyphenyl)-5-methyl-2-[N-(1-methoxycarbonylmethylindol-5-yl)-N-propylamino]thiazole,
4-(2-chloro-4-methoxyphenyl)-5-methyl-2-[N-(6-methoxyisoquinol-5-yl)-N-propylamino]thiazole oxalate,
4-(2-chloro-4-methoxyphenyl)-5-methyl-2-[N-(6-chloroisoquinol-5-yl)-N-propylamino]thiazole oxalate,
4-(2-chloro-4-methoxyphenyl)-5-methyl-2-[N-(6-methoxyisoquinol-5-yl)-N-propylamino]thiazole oxalate,
4-(2-chloro-4-methoxyphenyl)-5-methyl-2-[N-(1-methoxynaphth-2-yl)-N-propylamino]thiazole,
4-(2-chloro-4-trifluoromethylphenyl)-5-methyl-2-[N-(6-methoxyisoquinol-5-yl)-N-propylamino]thiazole oxalate,
4-(2-chloro-4-methoxyphenyl)-5-methyl-2-[N-(2-ethoxynaphth-1-yl)-N-propylamino]thiazole hydrochloride,
4-(2-chloro-4-methoxyphenyl)-5-methyl-2-[N-(2,3-dimethyinaphth-1-yl)-N-propylamino]thiazole hydrochloride,
4-(2-chloro-4-methoxyphenyl)-5-methyl-2-[N-(6-bromo-2-methoxynaphth-1-yl)-N-propylamino]thiazole hydrochloride,
4-(2-chloro-4-methoxyphenyl)-5-methyl-2-[N-(2,6-dimethylnaphth-1-yl)-N-propylamino]thiazole hydrochloride,
4-(2-chloro-4-methoxyphenyl)-5-methyl-2-[N-(1-(methoxymethyl)-1-(naphth-2-yl)methyl)-N-propylamino]thiazole hydrochloride,
4-(2-chloro-4-methoxyphenyl)-5-methyl-2-[N-(1-(cyclopropyl)-1-(naphth-2-yl)methyl)-N-propylamino]thiazole hydrochloride, of said compound, a stereoisomer of said compound, an addition salt of said compound, and a combination, thereof.

8. A process for the preparation of the compounds of formula (I) according to claim 1, wherein a substituted α-halogenated compound of formula (II)

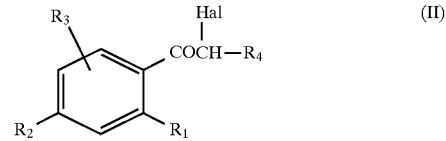

in which $R_1$, $R_2$, $R_3$, Hal and $R_4$ are as defined for (I), is reacted
either with a thiourea (ROUTE B) of formula:

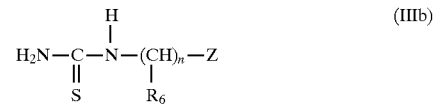

in which $R_6$ and Z are as defined for (I), to obtain a compound of formula (IV)

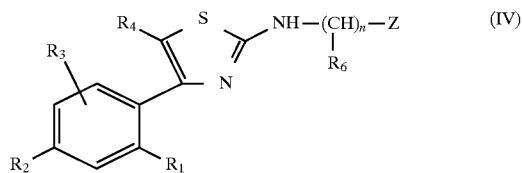

in which $R_1$, $R_2$, $R_3$, $R_4$, n, $R_6$ and Z are as defined for (1), in order to subsequently subject it to an alkylation reaction in order to provide the compound (I) and to obtain, in particular in the case where Z represents a nitrogenous heterocycle,
either monoalkylated compounds, the reactive nitrogen of the ring being first substituted by a protective group, -or dialkylated compounds, the freed reactive nitrogen being alkylated after deprotection of the ring of the monoalkylated compound obtained, it being possible for these dialkylated compounds, depending on the nature of the second alkyl group, to result in dialkylated products having different or identical alkyl groups, it being possible, in the latter case, for these compounds also to be obtained directly by dialkylation from the compound (IV) in which the reactive nitrogen of the heterocycle is not protected,
or with a thiourea (ROUTE A) of formula:

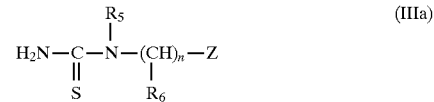

in which $R_5$, n, $R_6$ and Z are as defined for (I) to obtain directly a compound of formula (I).
or with thiourea (ROUTE C), to result in the aminothiazole of formula

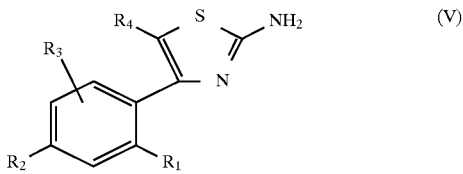

in which $R_1$, $R_2$, $R_3$ and $R_4$ are as defined for (I), which is then optionally reacted with an aldehyde of formula HCO-Z in order to obtain an imine which, by reacting with an organomagnesium compound or an organolithium compound of formula $R_6Li$ or $R_6MgX$ (where X is a halide), results in a compound of formula (IV) which is alkylated, by reacting it with a compound of formula $R_5X$ (where X is a leaving group), to obtain the compound (I) and, if appropriate, the compounds of formula (I) thus obtained are then optionally separated into their possible stereoisomers and/or salified to form the corresponding salts.

9. A method for the treatment of diseases requiring modulation of the effect of corticotropin releasing factor comprising administering to a person in need thereof an effective amount of a compound of formula (I) according to claim 1 in combination or with a pharmaceutically acceptable, inert excipient.

10. Pharmaceutical composition containing, as active principle, at least one compound according to claim 1, or a salt, thereof, with a pharmaceutically acceptable inorganic or organic acid, in combination with a pharmaceutically acceptable, inert excipient.

* * * * *